(12) United States Patent
Ben-Nun et al.

(10) Patent No.: US 9,532,903 B2
(45) Date of Patent: *Jan. 3, 2017

(54) CIRCULAR THERMAL CAPSULOTOMY TOOL AND SYSTEM

(75) Inventors: Joshua Ben-Nun, Moshav Beit Herut (IL); Adam Lerer, Herzlia (IL)

(73) Assignee: Valens Associates, Inc., Urbanizacion Obarrio (PA)

(*) Notice: Subject to any disclaimer, the term of this patent is extended or adjusted under 35 U.S.C. 154(b) by 331 days.

This patent is subject to a terminal disclaimer.

(21) Appl. No.: 14/005,560

(22) PCT Filed: Mar. 21, 2012

(86) PCT No.: PCT/IL2012/000126
§ 371 (c)(1),
(2), (4) Date: Nov. 20, 2013

(87) PCT Pub. No.: WO2012/127465
PCT Pub. Date: Sep. 27, 2012

(65) Prior Publication Data
US 2014/0074088 A1    Mar. 13, 2014

Related U.S. Application Data

(63) Continuation-in-part of application No. 13/053,259, filed on Mar. 22, 2011, now Pat. No. 8,657,813, which
(Continued)

(51) Int. Cl.
*A61B 18/12* (2006.01)
*A61F 9/007* (2006.01)
(Continued)

(52) U.S. Cl.
CPC ......... *A61F 9/00754* (2013.01); *A61B 18/082* (2013.01); *A61B 2017/00973* (2013.01);
(Continued)

(58) Field of Classification Search
CPC ................... A61B 18/082; A61B 2017/00973; A61B 2018/00196; A61F 9/00754
(Continued)

(56) References Cited

U.S. PATENT DOCUMENTS 4,766,897 A    8/1988 Smirmaul
5,269,787 A    12/1993 Cozean, Jr. et al.
(Continued)

FOREIGN PATENT DOCUMENTS

IL    WO 2006/109290    10/2006
WO    PCT/IL05/000461    11/2006

*Primary Examiner* — Daniel Fowler
(74) *Attorney, Agent, or Firm* — Edward Langer Adv. & Patent Attorney

(57) ABSTRACT

A system and tool for performing a capsulotomy procedure. The system includes a capsulotomy and movement control unit providing electrical current and movement control, and a capsulotomy tool, and an extendable-retractable burning element coupled to the tool, and a slidable shaping element. A capsulotomy and movement control unit provides electrical current to the burning element and movement control for extending and retracting the burning element. When the burning element is in a flattened, retracted configuration, the tip of the tool can be inserted through a relatively small corneal incision. Then, the burning element is opened to a full circular, extended configuration, by pressing the shaping element against both joints of the bands, allowing a capsulotomy by applying an electrical pulse to the burning element.

42 Claims, 25 Drawing Sheets

Related U.S. Application Data is a continuation-in-part of application No. 12/013,488, filed on Jan. 14, 2008, now Pat. No. 8,235,978, which is a continuation-in-part of application No. 11/911,111, filed on Mar. 11, 2009, now Pat. No. 8,162,931.

(51) Int. Cl.
*A61B 18/08* (2006.01)
*A61B 17/00* (2006.01)
*A61B 18/00* (2006.01)
*A61F 9/008* (2006.01)

(52) U.S. Cl.
CPC ............... *A61B 2018/00196* (2013.01); *A61F 2009/00889* (2013.01)

(58) Field of Classification Search
USPC .................................................... 606/27–31
See application file for complete search history.

(56) References Cited

U.S. PATENT DOCUMENTS

| | | |
|---|---|---|
| 5,873,883 A | 2/1999 | Cozean, Jr. et al. |
| 6,066,138 A | 5/2000 | Sheffer et al. |
| 7,125,424 B2 | 10/2006 | Banick |
| 2010/0145447 A1 | 6/2010 | Jia et al. |
| 2010/0179544 A1 | 7/2010 | Boukhny |

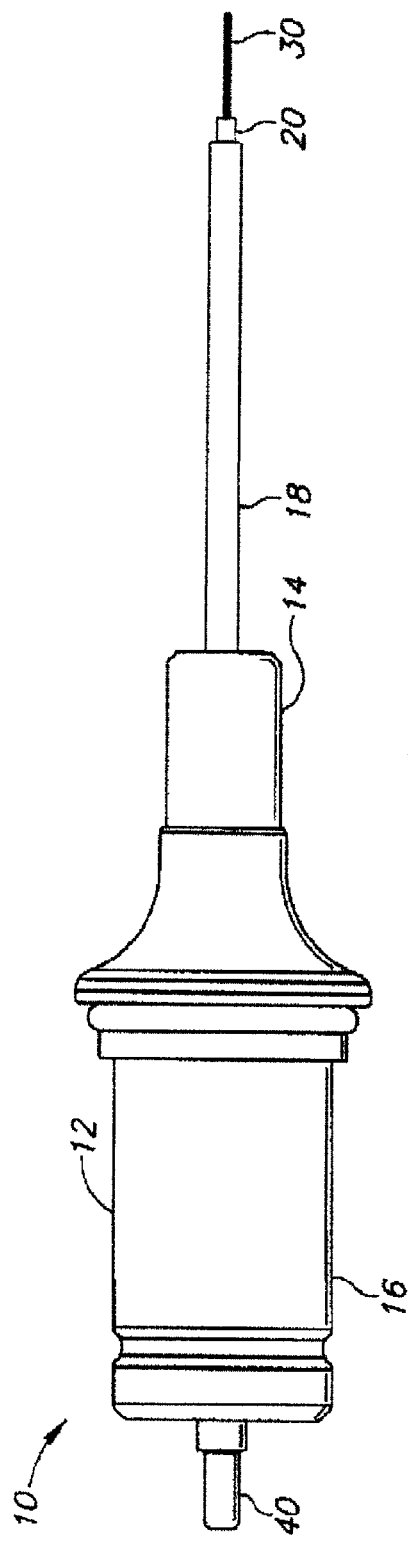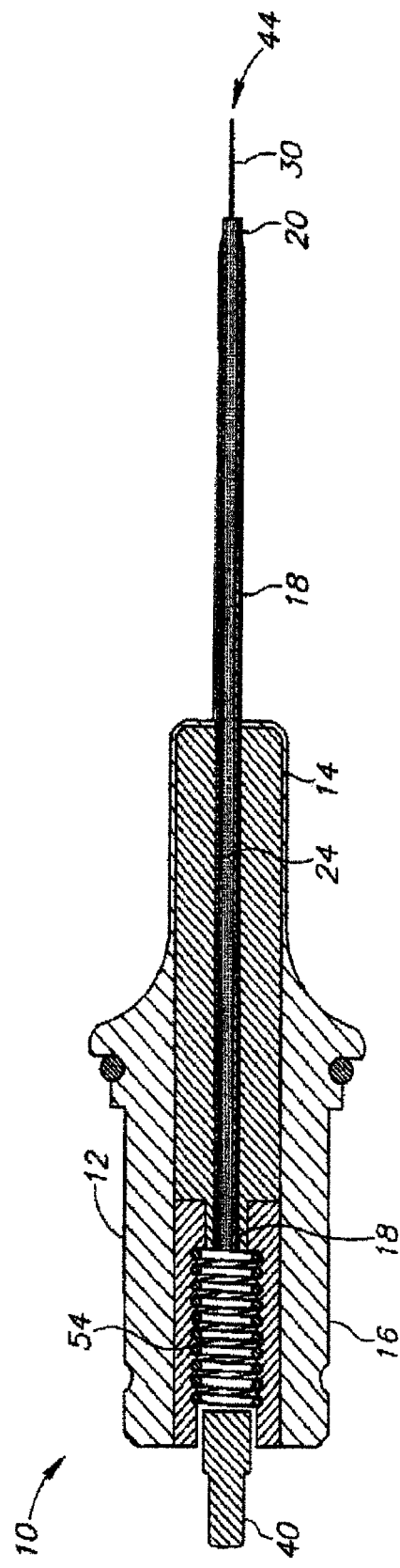

VIEW A-A

CIRCULAR THERMAL CAPSULOTOMY TOOL AND SYSTEM

FIELD OF THE INVENTION

The present application is a National Stage application based on PCT/IL2012/000126 and Continuation-in-part of application Ser. No. 13/053,259 filed on Mar. 22, 2011, which is a continuation-in-part of application Ser. No. 12/013,488, filed Jan. 14, 2008, now U.S. Pat. No. 8,235,978, which is a continuation-in-part of application Ser. No. 11/911,111, filed Mar. 11, 2009, now U.S. Pat. No. 8,162,931.

The present invention relates to the field of cataract surgery. More specifically, the present invention relates to a system and tool for performing a capsulotomy procedure.

BACKGROUND OF THE INVENTION

To date, over one million cataract surgeries are performed annually in the United States, in which the anterior lens capsule must be opened to gain access to the lens nucleus and allow removal of degenerated cortical material. It is necessary to create a relatively large circular opening in the lens capsule in order to enter the lens interior and to withdraw matter from inside. Formation of this opening is known as a capsulotomy. It is important that the opening has smooth edges and is tear resistant so that the lens contents can be easily removed through the opening. The lens opening is usually on the order of 4-7 millimeters in diameter, though this may vary.

Currently, two techniques for anterior capsulotomy are widely used: the "can-opener" technique and capsulorrhexis. In can-opener capsulotomy, a small incision in the sclera or peripheral cornea is performed, then a cystotome, knife, or needle is inserted through the incision and small connecting tears are made in the anterior lens capsule in a circular pattern. After a complete circle has been made by connecting the tears, a circular piece of the anterior capsule is grasped with forceps and torn away along the perforations. Unfortunately, when opening the capsule with numerous small capsular tears, the small tags that remain become a focal area of least resistance and can lead to tears, which extend radially and posteriorly to the posterior capsule. The detrimental result is a loss of structural stability of the capsule and an increased likelihood of vitreous entry into the anterior chamber.

Capsulorrhexis denotes a circular central opening in the anterior capsule. This continuous opening eliminates the residual tags common with the can-opener technique described above. In capsulorrhexis, a capsular incision is made with a cystotome, and this incision is coaxed to form a circular shape by pushing the leading edge of the freshly tearing capsule with the cystotome in a non-cutting fashion or by grasping the leading edge with forceps. This procedure is challenging for the surgeon to control. The tearing motion can lead to an undesirable tear toward the equator and the posterior capsule, and the size of the opening is difficult to dictate. Capsulorrhexis requires a significant amount of skill and experience and to consistently obtain successful results.

Opening the anterior capsule via either of the described techniques of anterior capsulotomy is a delicate procedure and is widely considered to be one of the most difficult steps in cataract surgery. A poorly performed anterior capsulotomy significantly hinders the subsequent surgical steps and increases the probability of operative complications. Complications resulting from a poor capsulotomy include zonular stress with subsequent breakage of the posterior capsule, vitreous loss, and large capsular tags preventing efficient lens removal. A poor capsulotomy also prevents placement of an intraocular lens in the capsular bag due to ill-defined capsular structures. The operative time is lengthened and patient discomfort can be increased, along with the risk of postoperative complications and decreased visual acuity results.

With either of the above-described techniques for anterior capsulotomy, the size or position of the capsular opening is often not ideal. The location, size, and configuration of the incision have important consequences. For example, an overly small capsular opening can impair the safe removal of the lens nucleus and cortex and prevent proper intraocular lens insertion into the lens capsule. In addition, a small or eccentric capsular opening places excessive stress on the lens capsule during surgery, placing the eye at risk for zonular and capsular breakage.

Certain devices have been proposed to overcome the problems associated with conventional anterior capsulotomy techniques. For example, U.S. Pat. No. 4,766,897 issued to Smirmaul, and U.S. Pat. Nos. 5,269,787 and 5,873,883 issued to Cozean Jr. et al. each disclose instruments that include circular cutting members for incising the anterior capsule. However, use of such devices in small incision cataract surgery is limited due to their size. Specifically, the anterior lens capsule of the eye is shielded by the cornea and sclera, such that a passage wound must be cut in the corneal or scleral tissue before any surgical apparatus can reach the anterior capsule. It is desirable to limit the width of the passage wound incised on the corneal tissue, preferably to 1-3 millimeters. A small wound decreases the scope of the surgical closing procedures, promotes rapid healing, minimizes astigmatism, reduces potential infections, and offers rapid visual rehabilitation. Therefore, the instrumentation employed in cataract surgery should be capable of passing through a small wound. Prior art cutting members cannot be passed through a small corneal incision of 1-3 mm.

Burning tools exist in which heat is concentrated at the tip, and the tip is made to contact and burn a surgical site. In use of such burning tools for cataract surgery, an incision is made in the cornea, and the tip of tool is inserted through the incision and brought into contact with the capsule, where it is activated to sear through the capsule. The use of prior art burning tools is restricted by the small size of the incision, as previously mentioned, which hampers introduction of a large tip having a circular shape of the appropriate size of the desired seared area.

PCT International application No. PCT/IL2005/000461 (Publication No. WO 2006/117772) by the present inventor, describes a burning ring present at an oblique angle on the end of a narrow-diameter shaft. The burning ring can therefore be introduced through a small incision, and the oblique angle grants a relatively large elliptical burn, with the largest axis of the burn being larger than the diameter of the shaft.

U.S. Pat. No. 6,066,138 to Sheffer et al. describes a searing cautery that is retractable from within a handle, so that the cautery can be extended to its final size after insertion through the corneal incision. The Sheffer patent suffers from the disadvantage that the burning ring does not close a complete circle, as apparent in FIG. 1b, with the area near the handle not being seared. Therefore, it is still necessary to grasp that remaining area with a forceps, and form a tear that is difficult to control. Additionally, since the searing ring is formed from a single metal wire extending substantially into the depths of the handle, when the wire is heated electrically, it is difficult to insulate the tool and prevent heating in unwanted areas. Searing could accidentally occur in other portions of the eye adjacent to the lens, since the handle of the tool could heat, and since the tool needs to be inserted considerably into the eye.

Other burning tools exist which have a small diameter tip, which is inserted through the incision, and used to burn a series of holes in the capsule, arranged in a ring, which is then grasped with forceps and torn into a circular opening. It is difficult to manipulate the burning tool to form a series of burns that are reliably ring-shaped and are present at the desired location, and form a ring of the desired size. Also, in cataract surgery, the procedure is usually complicated by the need for multiple instruments: a cutting tool, a water pressure inlet, means for retaining the shape of the cornea and related surgical and electrical equipment.

PCT International Application No. PCT/IL2006/000384 (Publication No. WO 06/109290) also by the present inventor, disclosed a surgical tool which provides both regulated heating and airflow pressure directed to a surgical site. The tool is capable of passing through a relatively small corneal incision and can easily form a large diameter ring-shaped opening in the capsule.

The tool overcame the need for multiple instruments in cataract surgeries as it provides both regulated heating and airflow pressure directed to a surgical site. Furthermore, the tool is convenient to handle, can be inserted through a small diameter (1-2.8 millimeters) incision in the cornea, and is capable of reliably creating a uniform circular-shaped opening of approximately 4-7 millimeters in the lens capsule. However, it is also known that air pressure may cause damage to the endothelial cells in the cornea, therefore it would be advantageous to use means other than air to maintain the structure of the cornea.

The surgical tool described in WO 06/109290, overcomes major problems associated with prior art tools. However, the scenario in which the tool breaks while in the eye was not addressed in the previous application by the inventor.

U.S. patent application Ser. No. 11/911,111 (CIP application) by the present inventor enlarges on the previous concept, describing a design aspect allowing straightforward removal of the tool from the eye in case of breakage of the tool during surgery, without damage to the eye.

SUMMARY OF THE INVENTION

Accordingly, it is a principal object of the present invention to provide a thermal system and tool for the performance of a capsulotomy that effects formation of an opening in the lens capsule through the use of a short pulse of electrical current. The heat generated from the current instantaneously burns an opening of a predetermined size in the lens capsule.

Additionally, the system and tool of the present invention has an expandable-retractable burning element that enables approaching the lens through a small corneal incision (about 1.5 millimeters) while allowing for a capsulotomy having a diameter, for example, of about 4-7 millimeters.

The present invention improves the previous tool, describing a design aspect allowing the bands of the burning ring to open into a full circular shape, as opposed to the previous quasi-circular shaped burning ring. The newly shaped burning ring generates a substantially full circular and therefore homogenous burn on the lens, thus preventing formation of weak points which may cause ripping of the lens. In addition, the present invention also produces increased temperature of the burning ring, thus creating a more complete cauterization of the lens, which in turn also prevents formation of weak points.

In accordance with a preferred embodiment of the present invention, there is provided a system for performing a capsulotomy procedure, comprising a capsulotomy tool further comprising a main housing having a distal end and an extendable-retractable burning element coupled to the distal end of the main housing and a capsulotomy and movement control unit. The capsulotomy tool is in connection with the capsulotomy and movement control unit for providing electrical current and movement control to the burning element such that when the burning element is extended and heated, an opening is burned on the lens capsule.

During the capsulotomy procedure, the shape of the cornea must be retained, so the cornea does not collapse. To this end, means for retaining the shape of the cornea must be used, externally to the inventive device, such as injection of any bio-compatible material to the eye, air flow directed into the eye, or any other means known by people skilled in the art.

According to a preferred embodiment of the present invention, the burning element comprises first and second electrically-conductive bands having opposite ends that are connected between the end of the inner rod and the tip of the outer tube. The bands have a height of approximately 50-250 nm greater than that of the inner rod, so that when the edges of the bands contact the lens, no other elements of the capsulotomy tool will contact it.

In a preferred embodiment, the first and second bands each have a groove upon them, with the groove representing a predefined point of weakness. In the undesirable scenario in which the electrical current is excessively high, breakage will occur at these predefined points of weakness. Should this occur while the tool is within the eye, the location of the grooves upon the bands is such as to nevertheless allow retraction of the broken bands from the eye. The tool can be immediately removed from the eye without damaging the eye. Preferably, a single groove is present on each band, and each groove is situated near the end of its respective band, close to the tip of the outer tube. The broken bands thus remain connected at the end of the inner rod, and can be retracted and removed from the eye.

Additionally, the system and tool of the present invention has a slidable shaping element connected to the outer tube extension by a pin inserted through a cavity formed in the shaping element, allowing the shaping element to push the bands into a full circular shape with a diameter of approximately 4-7 mm. The shaping element may be connected to the outer tube by any other suitable connecting means.

According to preferred embodiments of the present invention, the system also comprises a handle for connecting between the tool and the capsulotomy and control unit. The burning element for performance of the capsulotomy is retracted from the capsulotomy tool portion beyond the handle, and this tool portion is for disposable, one-time use.

In accordance with another preferred embodiment of the present invention, there is provided a tool for performing a capsulotomy, comprising;
(a) a main housing having a proximal end and a distal end;
(b) an extendable-retractable burning element for burning a lens, said burning element being coupled to said distal end of said main housing and adapted for being switched between a retracted configuration and an extended configuration;
(c) an inner rod extending longitudinally through said main housing and extending from the distal end of said main housing, wherein said burning element is positioned at the end of said inner rod;

(d) an outer tube that extends longitudinally through said main housing and that extends from said distal end of said main housing, wherein said inner rod is disposed inside of said outer tube;

(e) a slidable shaping element, connected to said outer tube so that said shaping element is slidable thereon and encompassed by said burning element, said shaping element providing shaping of said burning element; and (f) capsulotomy and movement control means coupled to the main housing for providing electrical current to the burning element and movement control for controlling extending and retracting of the burning element, wherein said retractable burning element is insertable into the eye through a small corneal incision when said burning element is in a retracted configuration, and said burning element is adapted to perform a capsulotomy of a predetermined size when it is in an extended configuration and an electrical current is applied to said burning element.

In accordance with another preferred embodiment of the present invention, the burning element comprises first and second electrically-conductive bands having their opposite ends, at the end of the outer tube, connected inwardly.

In accordance with another preferred embodiment of the present invention, the burning element comprises a single band.

In accordance with yet another preferred embodiment of the present invention, the burning element comprises first and second electrically-conductive bands having both their opposite ends overlapping each other, so as not to develop a gap between the blades and to create a circular burn on the lens having a closed continuous perimeter.

In accordance with a further preferred embodiment of the present invention, the burning element comprises a closed ring soldered on one side to the outer tube and on the other side to the inner rod, so as to create a circular burn on the lens having a closed continuous perimeter all along the ring.

In accordance with another preferred embodiment of the present invention, there is an orientation point located on the outer tube, situated in the center of the open ring, which will assist the tool-user in deciding where to place the burning ring before cauterization, In accordance with another preferred embodiment of the present invention, the burning element comprises first and second electrically-conductive bands, having each band constructed of three blades while the middle blade has a reduced width with respect to the outer blades and is also positioned higher than the outer blades. The reduced width of the middle blade increases its electrical resistance thereby increasing the heat transfer of the middle blade which closely contacts the lens for effective cauterizing. The temperature of the two outer blades is lowered by contact with the viscous matter in the eye. The viscous matter cannot seep in between the blades, and so the temperature of the middle blade remains high, higher than the temperature of the two outer blades. In effect, the outer blades function, also, as insulation to the middle blade.

Each of the three blades of the bands is narrower than the single blade according to an alternative embodiment of the present invention, a characteristic which allows more flexibility to the blades. This flexibility feature reduces the risk of cracks forming on the blades caused by repeated stretching when the burning element is opened to the extended configuration. Also, due to the narrowness of the blades, the bending radius is smaller than the radius of the single blade, which causes the bands to bend more so the joints of the bands are more flattened which enables the bands to assume a more complete circular shape.

In order to avoid any thermal damage to the ocular tissue surrounding the burning ring during capsulotomy, by direct contact or conducted heat, the two outer blades are each coated by a thermal biocompatible insulation material, in order to keep their temperature under 41° C. Due to the thermal insulation material, the heat from the outer blades is directed only downwards towards the eye capsule, and not towards the sides, where they might contact the Iris and then sear it and possibly damage it.

The blade coating is particularly effective when capsulotomy is performed in eyes with limited pupillary response for pharmacological dilatation. Normally, before cataract surgery the pupils must be dilated by pharmacological agents in form of eye drops to enable free access to the lens capsule. Some eyes have limited reaction to these drops with insufficient dilatation of the iris that results in a pupil size smaller than 6.0 mm. In such cases it is very difficult to perform any kind of capsulotomy including capsulorrhexis. The iris must be mechanically pulled during the beginning of the surgery by special iris retractors to expose the lens capsule surface and perform capsulorrhexis or laser capsulotomy. Since the temperature at the coated burning ring outer surface is safely below 41° C., the burning ring itself, when transformed from an elongated to round shape, pushes the iris edge aside, allowing the surgeon to perform a capsulotomy.

In accordance with another preferred embodiment of the present invention, the burning element comprises first and second electrically-conductive bands, having each band constructed of two blades, an inner blade and outer blade, while the inner blade has a reduced width with respect to the outer blade and is also positioned higher than the outer blade.

An additional feature of the preferred embodiment of the present invention, is a groove formed on the inner rod, which increases the electrical resistance at the point where the two bands overlap each other, so as to increase the temperature of that point, so proper and complete cauterization can be achieved.

A further additional feature of the present invention, is a pattern of the wave form of the electrical pulses applied for heating the burning ring, which improves the effectiveness of the cauterization. Before the main pulse which performs the cauterization, there are a series of pre-pulses, in variable numbers and voltages, which dry the area and pre-heat it, so that when the final pulse is activated, the cauterization, will be all the more effective and complete.

The cauterization may be performed with none of the pre-pulses, or with many of them, with different time gaps in between each pre-pulse.

Other features and advantages of the present invention will become more readily apparent and understood from the detailed description section that follows.

BRIEF DESCRIPTION OF THE DRAWINGS

For a better understanding of the invention with regard to the embodiments thereof, reference is made to the accompanying drawings, in which like numerals designate corresponding elements or sections throughout and in which:

FIG. 1 is a side view of a capsulotomy tool, according to a preferred embodiment of the present invention;

FIG. 2 is a cross-sectional side view of a capsulotomy tool, according to a preferred embodiment of the present invention;

FIG. 12b is a larger view of FIG. 12a;

FIG. 12d is a side view of a capsulotomy tool of FIG. 12a;

DETAILED DESCRIPTION OF THE PREFERRED EMBODIMENTS

Figure 3:
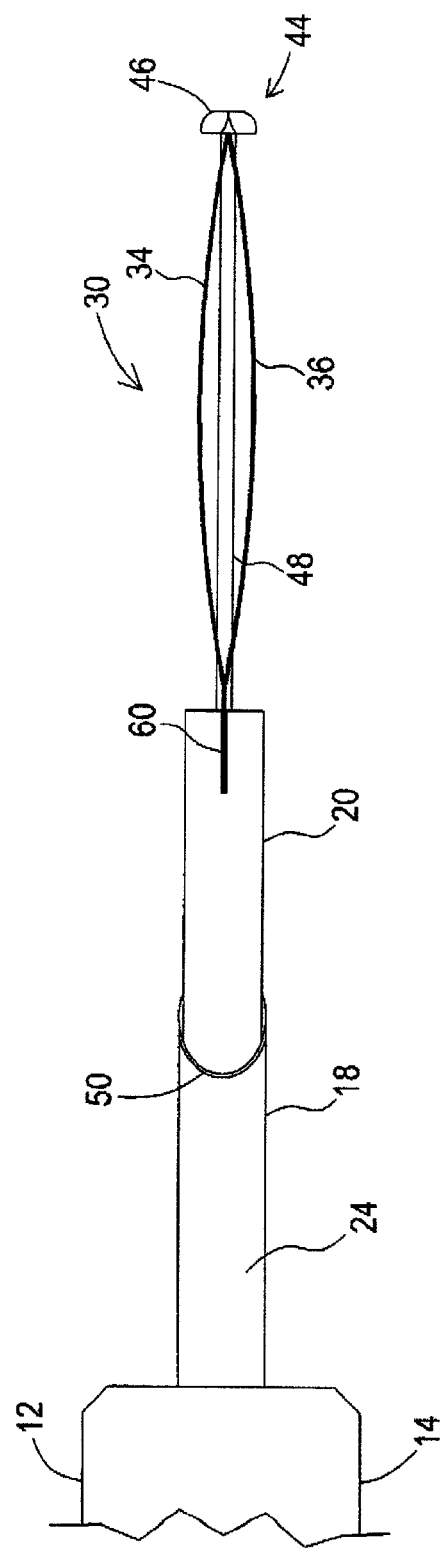
FIG. 3 is a partial cross-sectional side view of the embodiment, showing the burning element of the tool in a completely retracted configuration.

The present invention discloses a capsulotomy tool, which has a retractable cautery ring, also known as a burning element. After the tool is inserted past the capsular incision, the burning element is fully opened to expand into a complete circular shaped cautery, which is then heated to sear the lens. The complete circular-shaped searing thus eliminates the need for tearing by forceps, which is potentially dangerous and difficult to perform.

In the invention, heating is limited to the burning element, so there is no danger of searing inappropriate areas of the eye. The retractable nature of the burning element allows it to be introduced through a small capsular incision, yet provides burning on the lens at a diameter larger than that of the small capsular incision.

FIGS. 1-6 show a preferred embodiment for a capsulotomy tool 10, constructed and operated in accordance with the principles of the present invention.

Referring to FIG. 1, capsulotomy tool 10 includes a main housing 12 having a distal end 14 and a proximal end 16. Main housing 12 includes a connector 40 at proximal end 16 for facilitating connection of main housing 12 to a handle which is operably connected to a capsulotomy and movement control unit for providing electrical current to capsulotomy tool 10. This will be described further herein with respect to FIGS. 10a-b.

Referring to FIG. 2 and best shown in FIG. 3, capsulotomy tool 10 includes an outer tube 18 having a distal end 44. End 44 comprises a tip 46 and an outer tube extension 48 having a truncated circumference that extends between the completely tubular region (region not having a truncated circumference) of outer tube 18 and tip 46. The region where outer tube 18 changes from a completely tubular construction to extension 48 has a beveled edge 50, which provides extra structural support for outer tube extension 48, so that extension 48 can be made as thin as possible. Beveled edge 50 may be beveled to any suitable angle, for providing maximal support to extension 48.

Capsulotomy tool 10 also includes an inner rod 20 that passes through the central axis of main housing 12, and that extends from distal end 14 of main housing 12 and through outer tube 18.

Referring to FIG. 2, both inner rod 20 and outer tube 18 are coupled to a spring mechanism 54 located in main housing 12, for enabling movement of inner rod 20 within outer tube 18. This will be described further herein. It will be noted that as shown in FIG. 2, inner rod 20 is positioned inside of outer tube 18.

According to a preferred embodiment, all elements shown in FIG. 2 are disposable, and are intended for a single use. This includes housing 12, spring mechanism 54, inner rod 20, outer tube 18, as well as burning element 30a (to be described herein below).

Referring to FIG. 3, an extendable-retractable burning element 30a is connected to the end of inner rod 20. FIG. 3 illustrates the burning element 30a in its retracted state.

Figure 6:
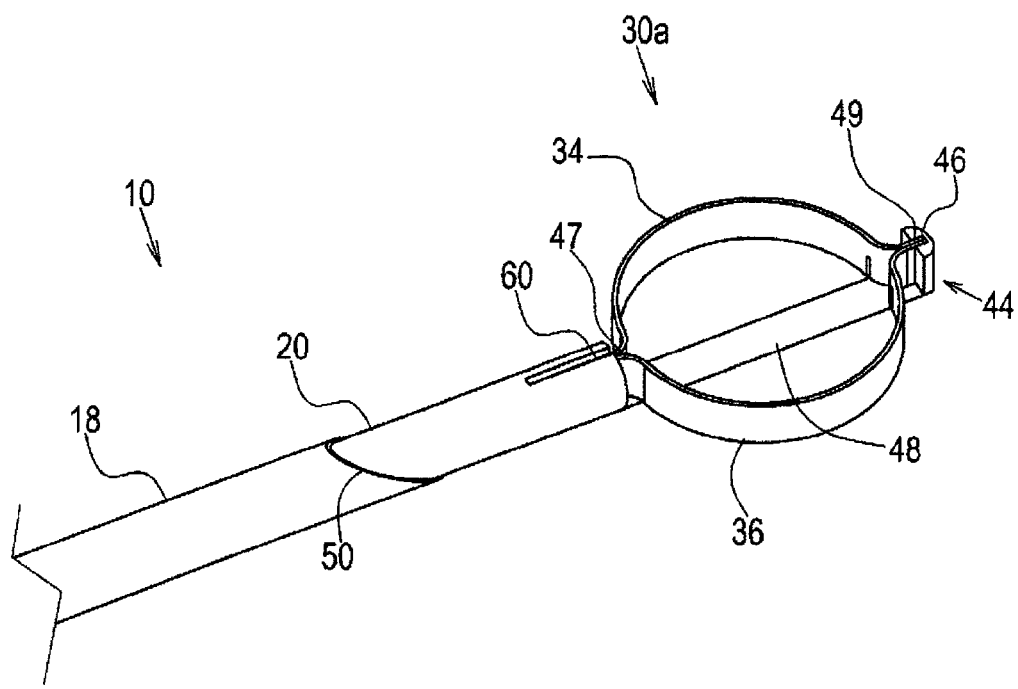
FIG. 6 is a partial view of a capsulotomy tool, showing the burning element in a completely opened configuration.

Burning element 30a includes a first band 34 and a second band 36, which are formed from biocompatible, electrically conductive material such as, though not limited to, a tungsten alloy. The opposite ends of each band 34, 36 are vertically connected at two points, herein referred to as joints, proximal joint 47 and distal joint 49, between the end of inner rod 20 and tip 46 of outer tube 18. Movement of inner rod 20 in the direction of tip 46 of outer tube 18 causes first band 34 and second band 36 to adopt the extended and open configuration, in which bands 34, 36 substantially form a circle with one another, as shown in FIG. 6. A spring mechanism 54 is provided for enabling movement of inner rod 20 and of outer tube 18. A brief pulse of electricity sent through the tool then causes bands 34, 36 of burning element to heat up and burn an opening in the lens capsule.

It will be appreciated that other mechanisms could be employed, as are well known in the art, for effecting outward movement of inner rod 20 and outer tube 18.

In the retracted configuration, bands 34, 36 of burning element 30a are positioned substantially flattened and parallel to one another, directly above extension 48 of outer tube 18. In FIGS. 1, 2 and 3, burning element 30a is in the retracted configuration (in FIG. 1, the burning element is not visible). In this position, the end of capsulotomy tool 10 can be inserted into a relatively small corneal incision, on the order of 1-2 millimeters.

Figure 4:
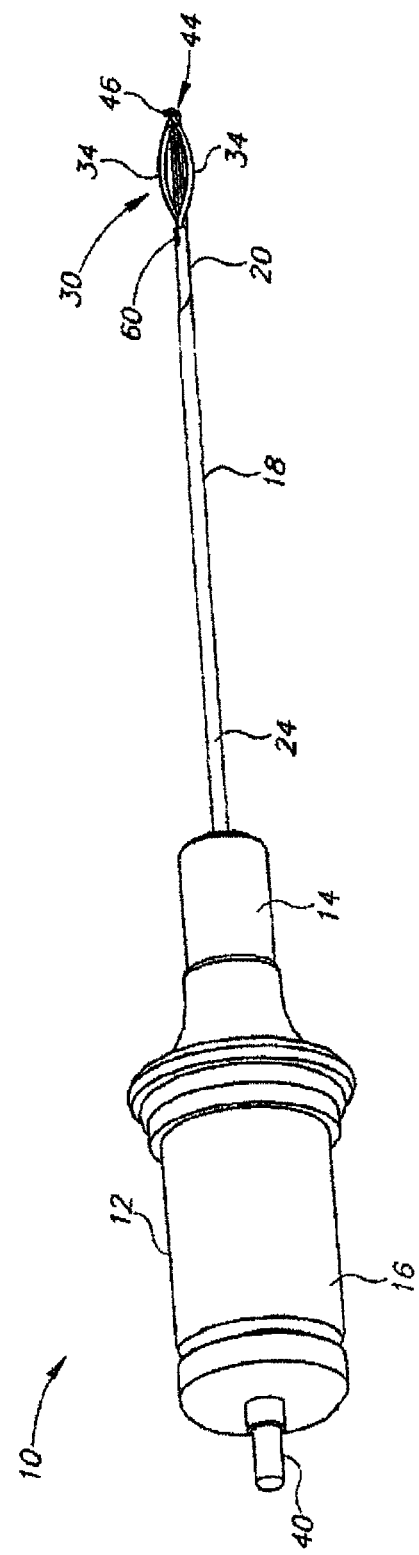
FIG. 4 is a perspective view of a capsulotomy tool, showing the burning element in an extended configuration.
Figure 5:
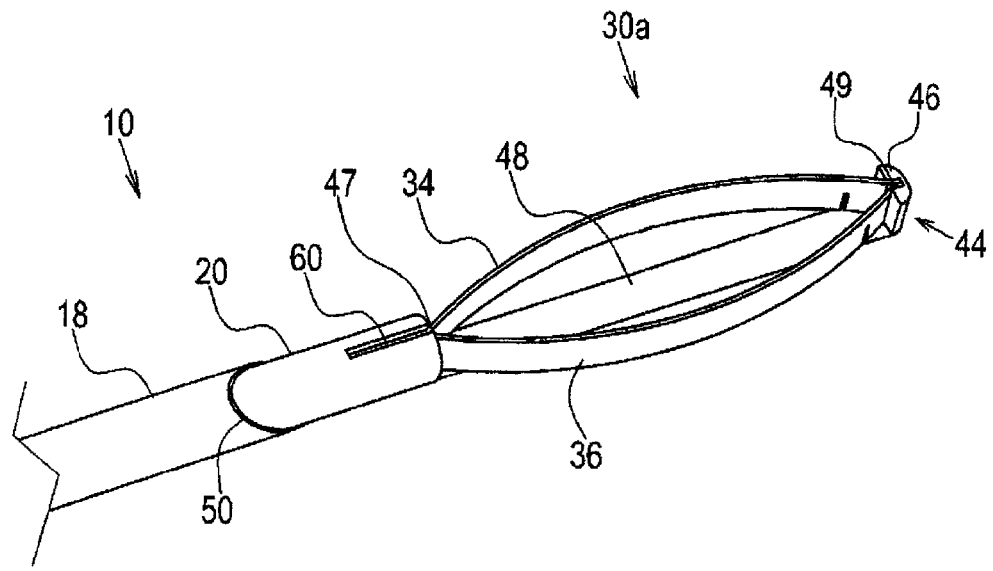
FIG. 5 is a partial view of a capsulotomy tool, showing an enlargement of the burning element in a partially opened configuration.

Referring to FIGS. 4-6, the extended and opened configuration is shown, though in FIG. 5, bands 34, 36 have been only partially opened.

The height of bands 34, 36 is approximately within the range of 50-200 microns higher than that of inner rod 20 and tip 46, so that when the edges of bands 34, 36 contact the capsule, no other elements of capsulotomy tool 10 will contact it. Inner rod 20 is provided with a slot 60 formed in the upper edge at the end thereof for accommodating the additional height of bands 34, 36.

The following drawings and description show the capsulotomy tool with an orientation featuring the cauterization side of the burning element.

Referring to FIGS. 5 and 6, the length of first and second bands 34, 36 is designed according to the size of the capsulotomy that is required. For example, for a capsulotomy of 4-5 millimeters, a band length of about 7 millimeters is required. The band length is approximately half the circumference of the required capsulotomy. Extension 48 of outer tube 18 must also be of sufficient length so as to accommodate bands 34, 36 when they are in the flattened, retracted configuration. The angle of beveled edge 50 can be made larger or smaller depending on the length of extension 48.

Optionally, before use the burning element 30a is removed from the tool 10, so that the size of the burning element can be selected in order to choose the size of the capsulotomy. Preferably, several removable burning elements can be designed having longer or shorter bands, in order perform a capsulotomy having a diameter selected from most preferred diameters between 4 to 7 mm. Removable burning elements of other sizes can also be envisioned.

First and second bands 34, 36 are formed from electrically conductive biocompatible material such as a tungsten alloy or any other suitable element. Inner rod 20 and outer tube 18, are both formed, at least partially, from electrically-conductive material. Extension 48 and tip 46 of outer tube 18, are likewise formed from the same material. Inner rod 20 and outer tube 18 define opposite poles of an electrical circuit, and they are designed so as to be electrically insulated from one another.

To perform a capsulotomy, a brief, low-voltage electrical pulse is passed through bands 34, 36. When a current is passed through inner rod 20, bands 34, 36, tip 46, extension 48, and returning through outer tube 18, bands 34, 36 will heat up (or vice versa depending on the polarity).

It will be appreciated that a switch is provided such that the electrical circuit can be completed only when burning element 30a is in the extended configuration, so as to prevent premature heating of burning element 30a.

Additional figures are now presented showing various constructions of the burning element, which are denoted as 30b, 30c, 30d, 30e, 30f, 30g, 30h, 30i, 30j and, 30k each of which are distinguished by their final shape and/or configuration of the opposite ends of the bands and/or the number of blades in each band.

Figure 7A:
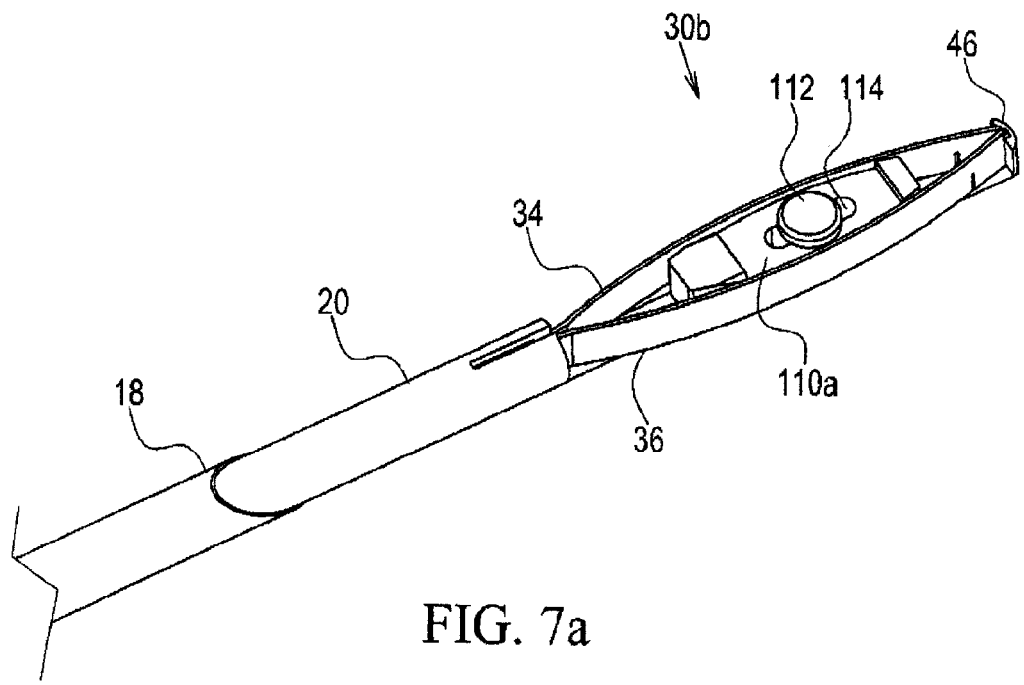
FIG. 7a is a partial view of a capsulotomy tool, showing an enlargement of the burning element in an initial configuration and featuring the shaping element.
Figure 7B:
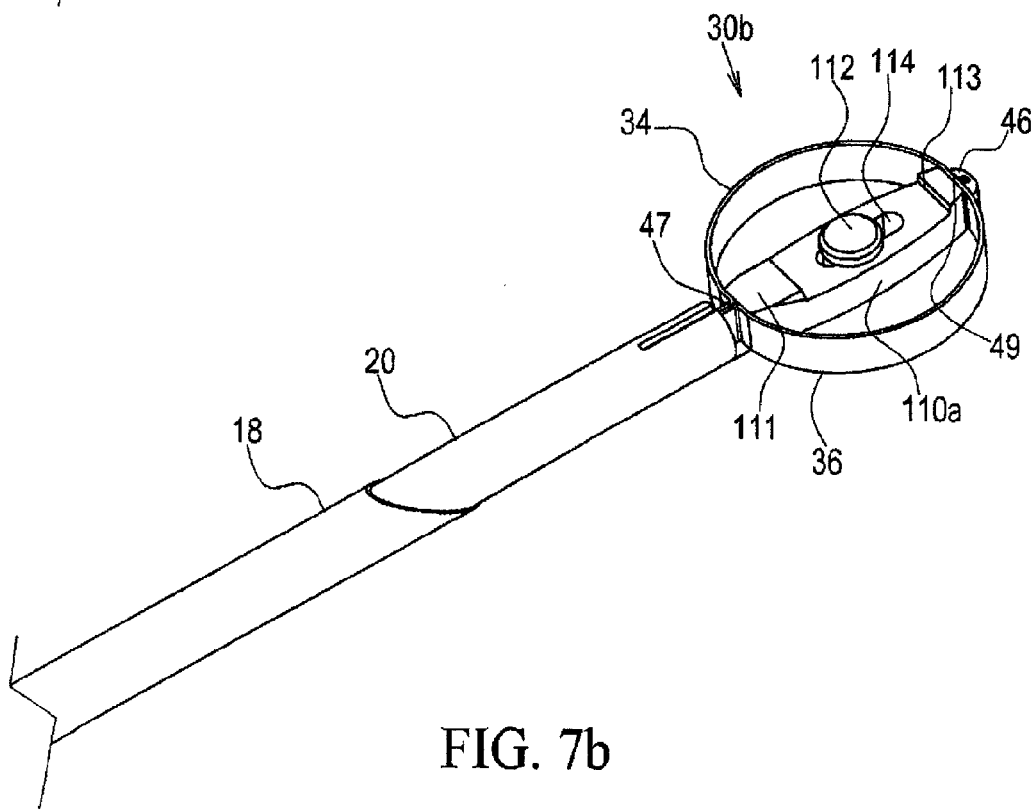
FIG. 7b is a partial view of a capsulotomy tool, showing an enlargement of the burning element in a completely opened configuration featuring the shaping element.

FIGS. 7a-7b show an alternative embodiment for a capsulotomy tool 10 constructed and operated in accordance with the principles of the present invention, with the addition of a slidable shaping element 110a for the purpose of achieving a substantially full-circular shaped burning element.

In FIG. 7b, inner rod 20 is moved towards tip 46 of outer tube 18, thereby causing bands 34, 36 to extend from inner rod 20. In this fashion, proximal joint 47 is pushed against proximal end 111 of shaping element 110a by sliding contact. Since pin 112 remains stationary, shaping element 110a advances along outer tube extension 48, until shaping element 110a reaches tip 46 and further movement is restricted. At this stage, the shape of distal end 113 of shaping element 110a presses against distal joint 49, and has the same radius as the circular configuration of bands 34, 36. Thus, each of bands 34, 36 is forced to assume a substantially full-circular configuration.

It will be appreciated by those skilled in the art that the size and shape of shaping element 110a may be modified to allow for other burning ring shapes (i.e. elliptical).

Figure 8:
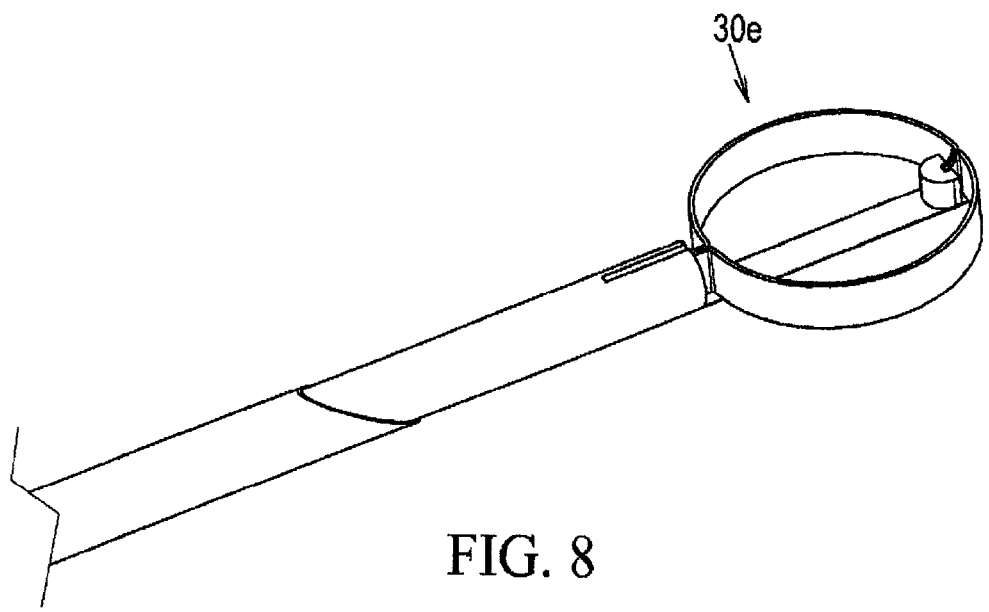
FIG. 8 is a partial view of a capsulotomy tool, showing the burning element in a completely opened configuration, while the joints of the blades are connected inwardly, according to a preferred embodiment of the present invention.

In FIG. 8, inner rod 20 is moved towards tip 46 of outer tube 18, in the same fashion as described in FIG. 7. In this particular embodiment, bands 34, 36 are joined inwardly to tip 46 of outer tube extension 48. This particular embodiment may or may not involve shaping element 110.

Figure 9:
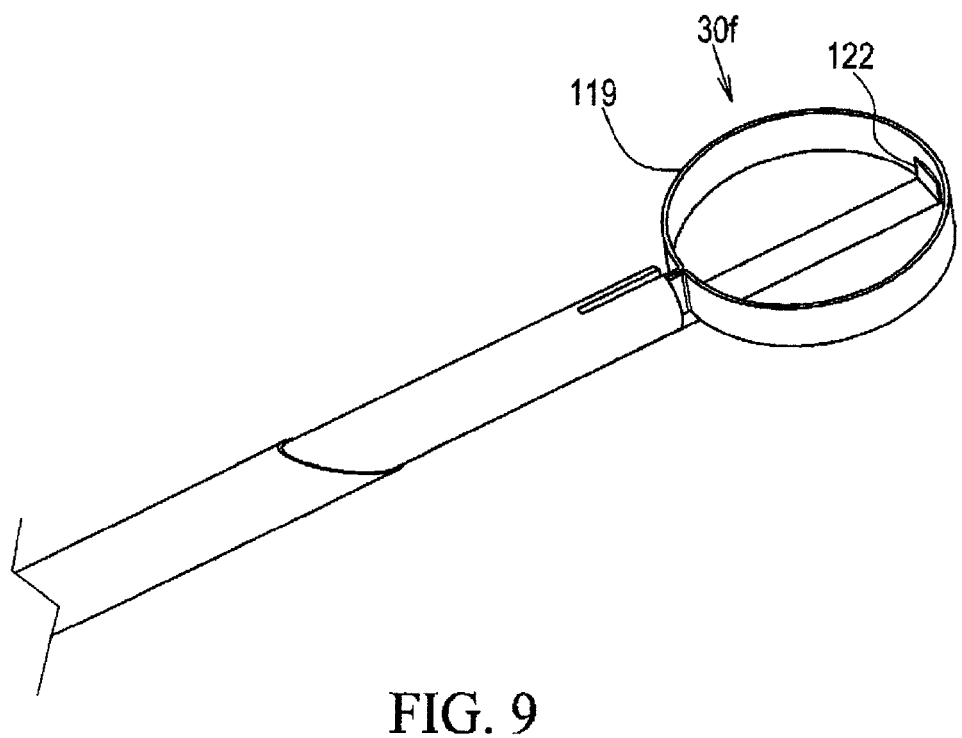
FIG. 9 is a partial view of a capsulotomy tool, showing the burning element as a single blade in a completely opened configuration, according to a preferred embodiment of the present invention.

In FIG. 9, inner rod 20 is moved towards tip 46 of outer tube 18, in a similar fashion described in FIG. 7. In this particular embodiment of the invention, burning element 30f is formed out of a single band 119 for generation of a circular burn having a closed continuous perimeter. A portion of the distal end of outer tube extension 48 is bent 90 degrees upwards forming a plate extension 122, which is soldered to band 119. While advancing burning element 30F along outer tube extension 48, plate extension 122 forces band 119 to assume a circular configuration. This particular embodiment may or may not involve shaping element 110.

Figure 10A:
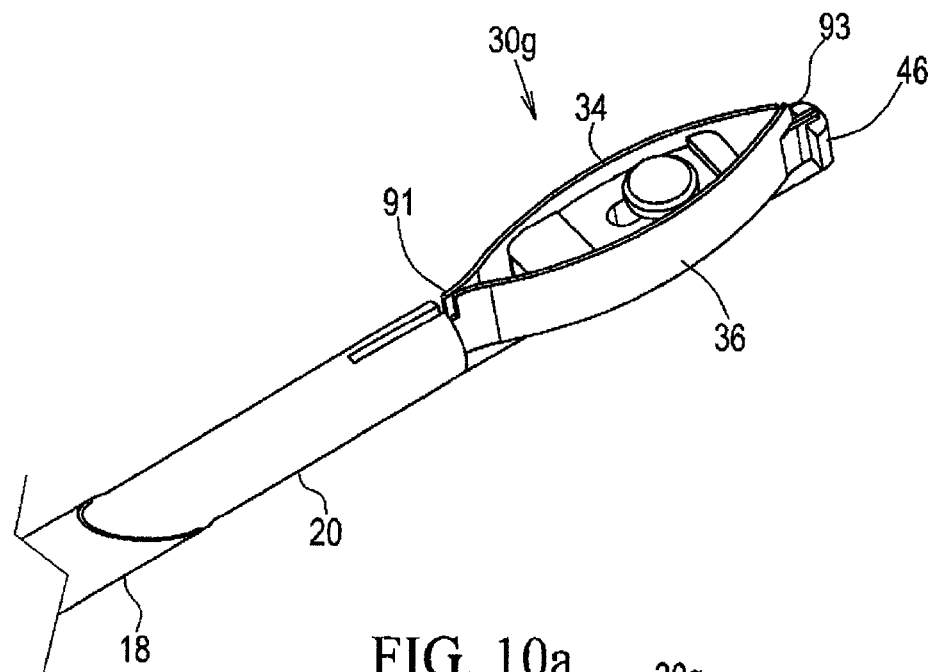
FIG. 10a is a partial view of a capsulotomy tool, showing the burning element in a partially opened configuration, while the blades overlap each other, according to a preferred embodiment of the present invention.
Figure 10B:
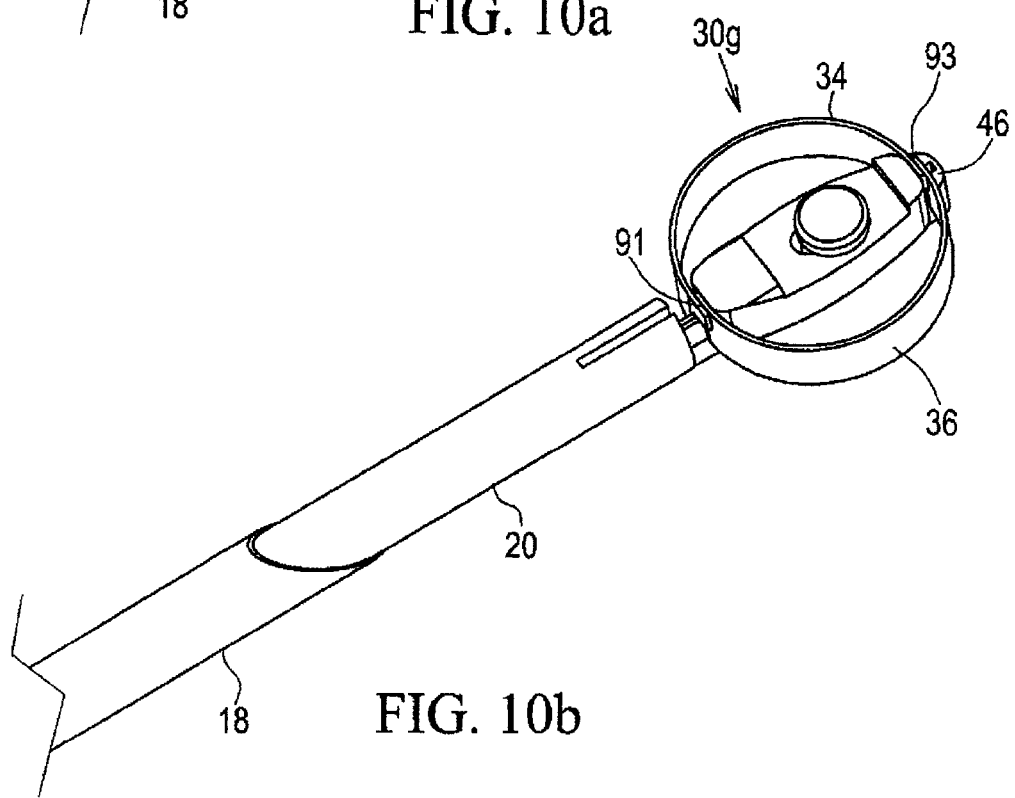
FIG. 10b is a partial view of a capsulotomy tool, showing the burning element in a completely opened configuration, while the blades overlap each other, according to a preferred embodiment of the present invention.

FIGS. 10a-10b show an alternative embodiment for a capsulotomy tool 10 constructed and operated in accordance with the principles of the present invention, with the two blades of burning element 30g overlapping each other on both ends for the purpose of generating a circular burn on the lens having a closed continuous perimeter.

In FIG. 1b, inner rod 20 is moved towards tip 46 of outer tube 18, in a similar fashion described in FIG. 7. In this particular embodiment of the invention, bands 34, 36 overlap each other at both their opposite ends, forming flag shaped regions 91 and 93. The bands overlapping eliminate the gap formed between them in previous embodiments, and by doing so, generating a circular burn on the lens having a closed continuous perimeter.

Figure 11A:
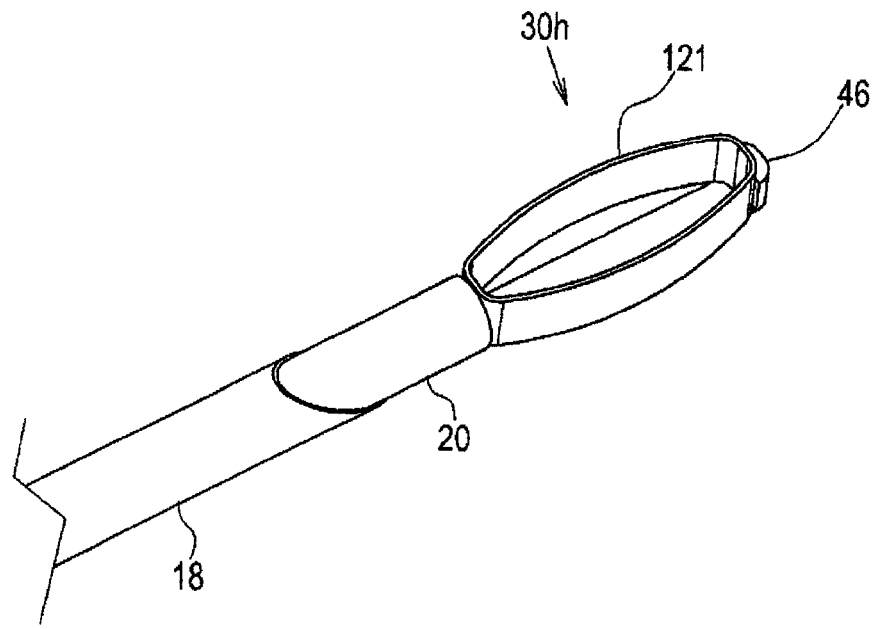
FIG. 11a is a partial view of a capsulotomy tool, showing the burning element in a partially opened configuration, while the burning element is made of a sealed, gapless ring.
Figure 11B:
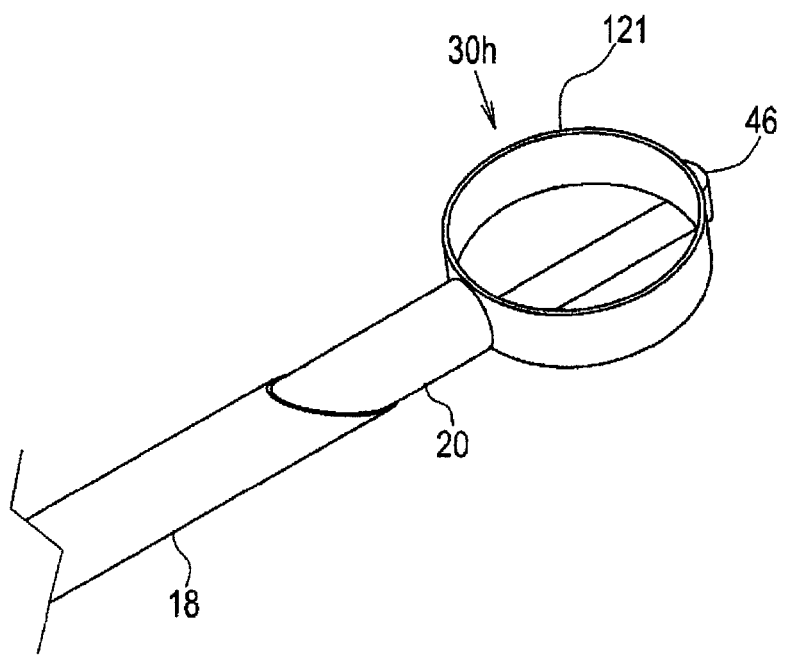
FIG. 11b is a partial view of a capsulotomy tool, showing the burning element in a completely opened configuration, while the burning element is made of a sealed, gapless ring.

FIGS. 11a-11b show an alternative embodiment for a capsulotomy tool 10 constructed and operated in accordance with the principles of the present invention, with the burning element 30h comprising of a sealed ring, for the purpose of generating a circular burn on the lens having a gapless, closed continuous perimeter all along the burn.

In FIG. 11b Inner rod 20 is moved towards tip 46 of outer tube 18, in a similar fashion described in FIG. 7. The burning element 30h is made of a ring 121 which is soldered on one side to inner rod 20 and on the other side to outer tube 18. The ring 121 is sealed, gapless and generates a burn on the lens having a closed continuous perimeter all along the burn.

FIGS. 12a-12e show an alternative embodiment for a capsulotomy tool 10 constructed and operated in accordance with the principles of the present invention, with the two bands 34, 36 of burning element 30i overlapping each other, and comprising of three blades each, for the purpose of increasing the heat transfer of the blades to achieve a more effective and complete cauterization.

Figure 12A:
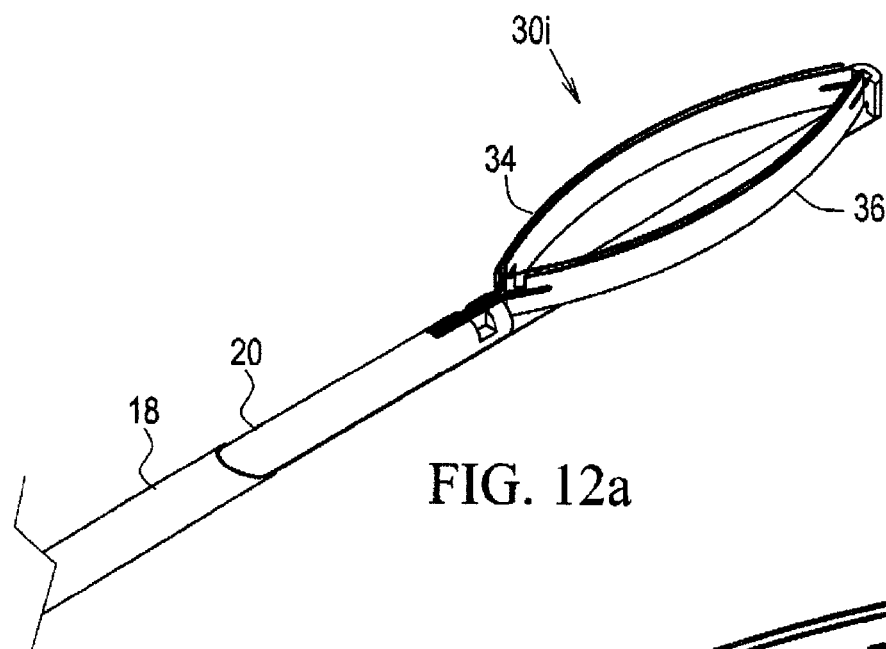
FIG. 12a is a perspective view of a capsulotomy tool, showing the burning element in a partially opened configuration, while the bands are each constructed of three blades, according to a preferred embodiment of the present invention.
Figure 12B:
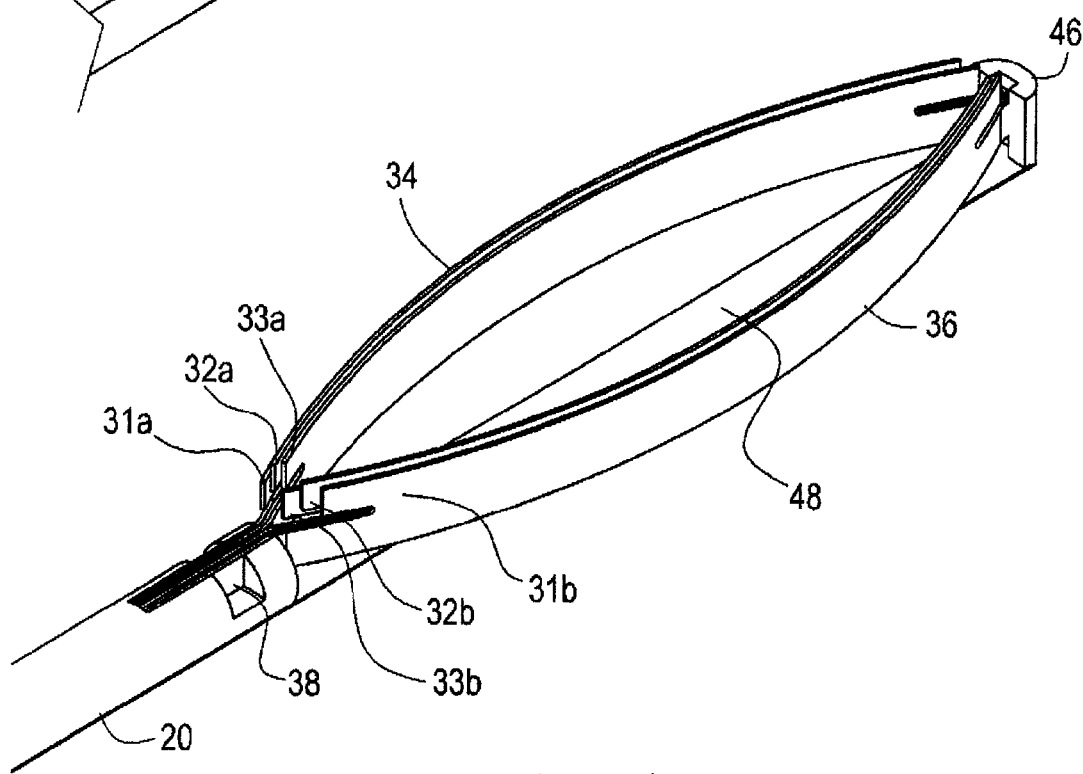
Figure 12C:
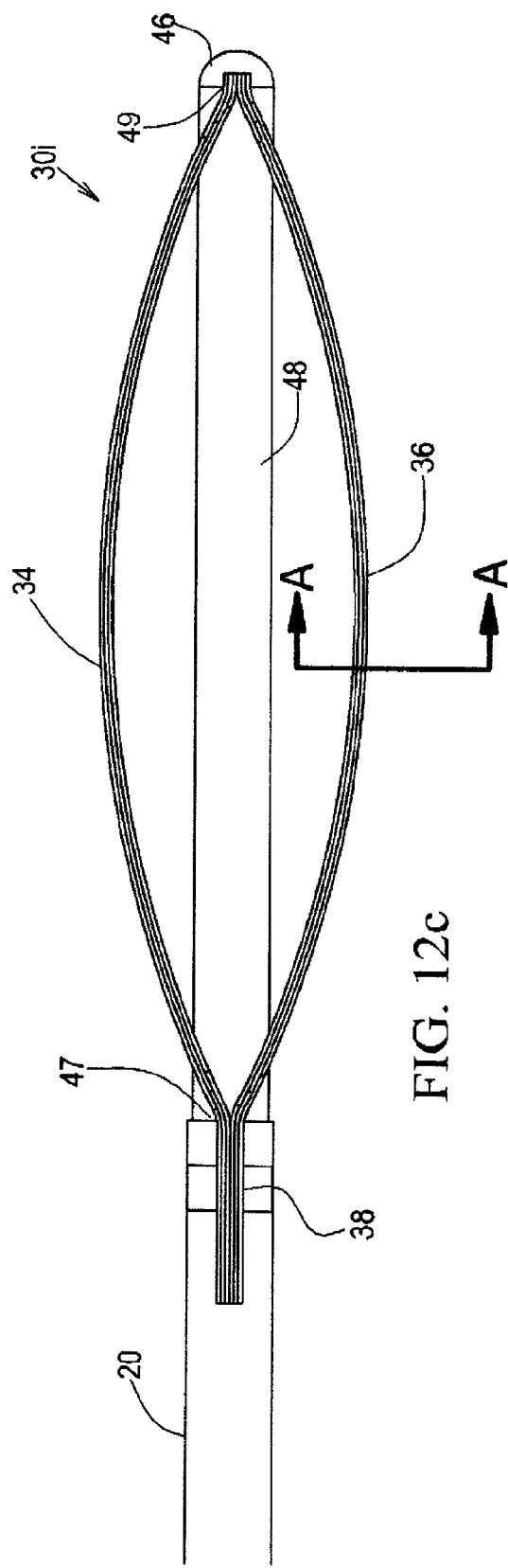
FIG. 12c is a partial top view of a capsulotomy tool of FIG. 12a showing the burning element in a partially opened configuration.
Figure 12D:
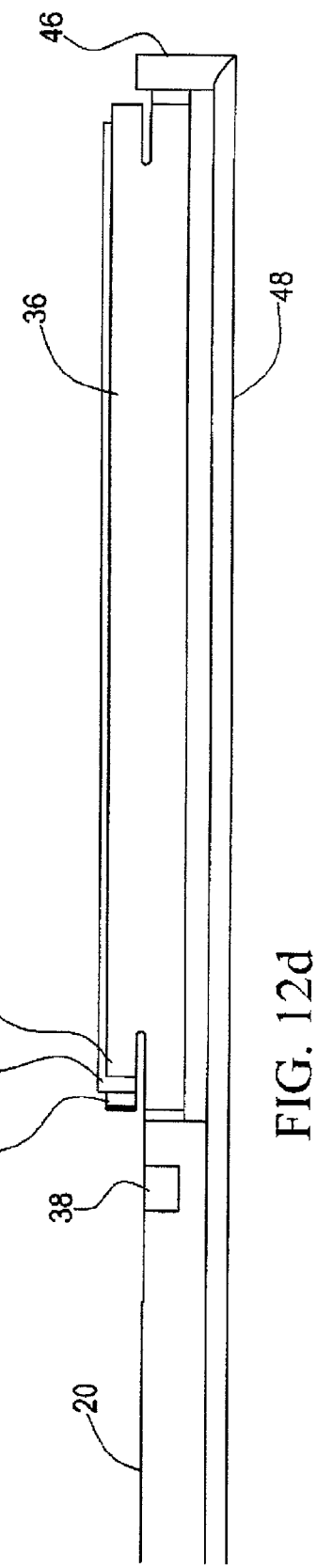

In FIGS. 12b-d at the distal end of inner rod 20 is a groove 38 created, which increases the electrical resistance at proximal joint 47, so as to increase the temperature of that point, so proper cauterization can be achieved.

Figure 12E:
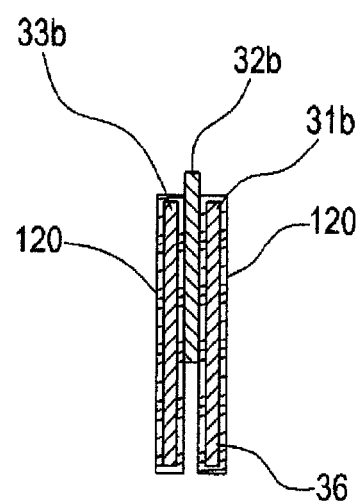
FIG. 12e is a cross-sectional view of one of the bands of the burning element of FIG. 12a, showing the thermal insulation material.

FIG. 12e shows a cross section of band 36 illustrating the width of both outer blades 31b, 33b is identical, while the width of middle blade 32b is smaller, and blade 32b is positioned higher than the outer blades. The thermal insulation 120 coating the outer side of blades 31b and 33b is indicated.

Figure 13A:
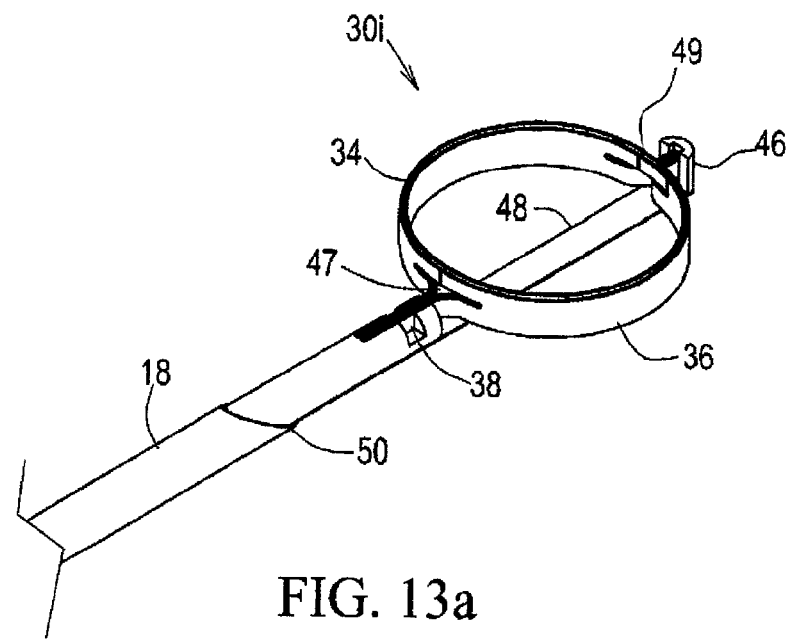
FIG. 13a is a perspective view of a capsulotomy tool of FIG. 12a showing the burning element in a completely opened configuration, while the blades overlap each other.
Figure 13B:
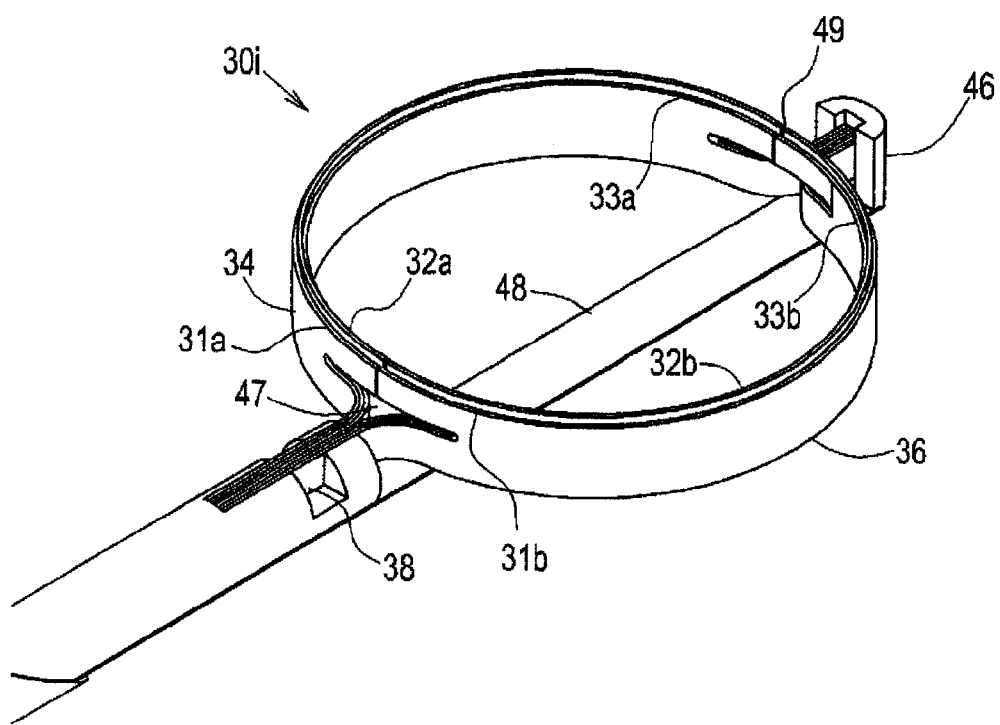
FIG. 13b is a larger perspective view of a capsulotomy tool of FIG. 12a showing the burning element in a completely opened configuration.
Figure 13C:
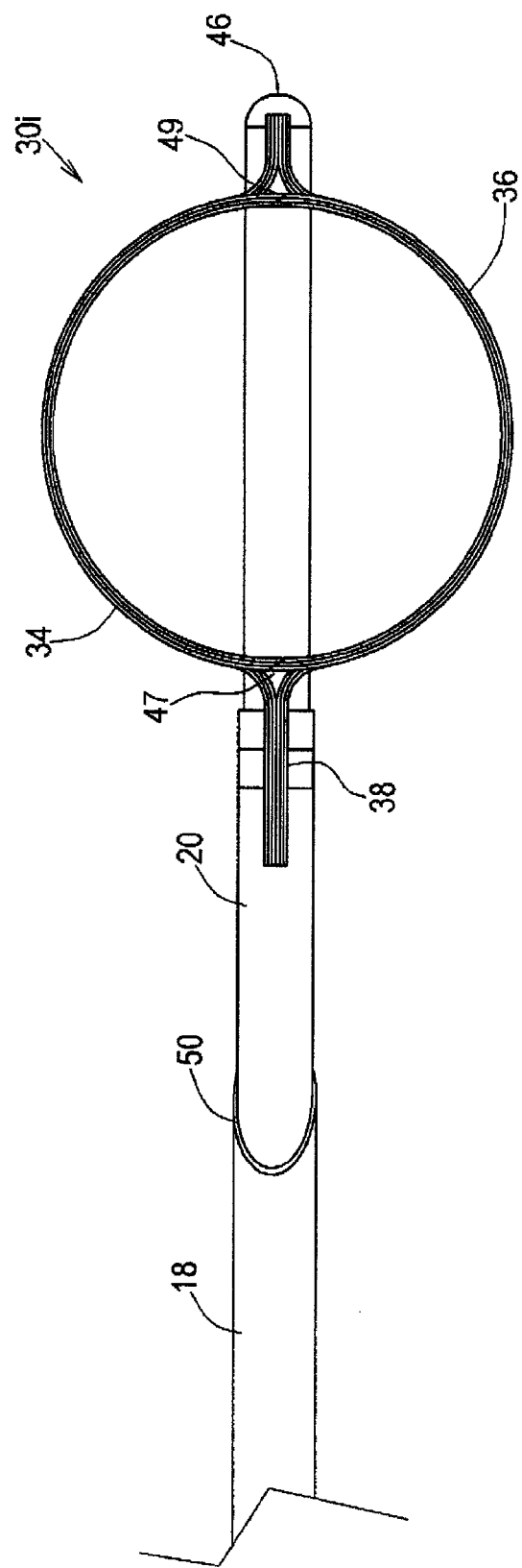
FIG. 13c is a partial top view of a capsulotomy tool of FIG. 12a showing the burning element in a completely opened configuration.

FIGS. 13a-c show the embodiment of FIG. 12 in a completely opened configuration. Inner rod 20 is moved towards tip 46 of outer tube 18, in a similar fashion described in FIG. 7. The burning element 30i is made of two bands 34, 36, when each of them are constructed of three blades 31a, 32a, 33a and 31b, 32b, 33b, respectively. The middle blades 32a, 32b of bands 34, 36 have a reduced width with respect to the outer blades 31a-b, 33a-b, so as to increase the electrical resistance which results in a higher temperature of middle blades 32a-b. Middle blades 32a-b are insulated by outer blades 31a-b, 33a-b, to protect middle blade 32a-b from becoming cooled down by the viscous matter in the eye. By protecting middle blade 32a-b from both sides, blades 31a-b, 33a-b come into contact with the viscous matter, which doesn't seep in between the blades, and get cooled by it, and middle blade 32a-b remains at a high temperature that is ideal for cauterizing. All this and the fact that the middle blades 32a-b are also positioned higher with respect to the outer blades 31a-b, 33a-b, so they contact the eye capsule more closely, and contribute to a more effective cauterization.

In order to avoid any thermal damage to the ocular tissue surrounding the burning ring 30 during capsulotomy, by direct contact or conducted heat, the two outer blades 31a-b, 33a-b are each totally coated by a thermal biocompatible insulation material 120 in order to keep their temperature under approximately 41° C. Due to the thermal insulation material 120, the heat from the outer blades 31a-b, 33a-b is directed only downwards towards the eye capsule, and not towards the sides, where they can contact the iris and then sear it and possibly damage it.

The blade coating is particularly effective when capsulotomy is performed in eyes with limited pupillary response for pharmacological dilatation. Normally, before cataract surgery the pupils must be dilated by pharmacological agents in form of eye drops to enable free access to the lens capsule. Some eyes have limited reaction to these drops with insufficient dilatation of the iris that results in a pupil size smaller than 6.0 mm. In such cases it is very difficult to perform any kind of capsulotomy including capsulorrhexis. The iris must be mechanically pulled during the beginning of the surgery by special iris retractors to expose the lens capsule surface and perform capsulorrhexis or laser capsulotomy. Since the temperature at the coated burning ring 30 outer surface is below approximately 41° C., the burning ring 30 itself; while transformed from elongated to round shape, pushes the iris edge aside, and opens it to the size of the expanded burning ring. This way, the pupils are at a sufficient size for allowing the surgeon to perform the capsulotomy.

In addition, due to the narrowness of each blade 31-33, approximately 0.2 mm each, the bending radius decreases, causing the burning element 30i to become rounder.

Figure 14A:
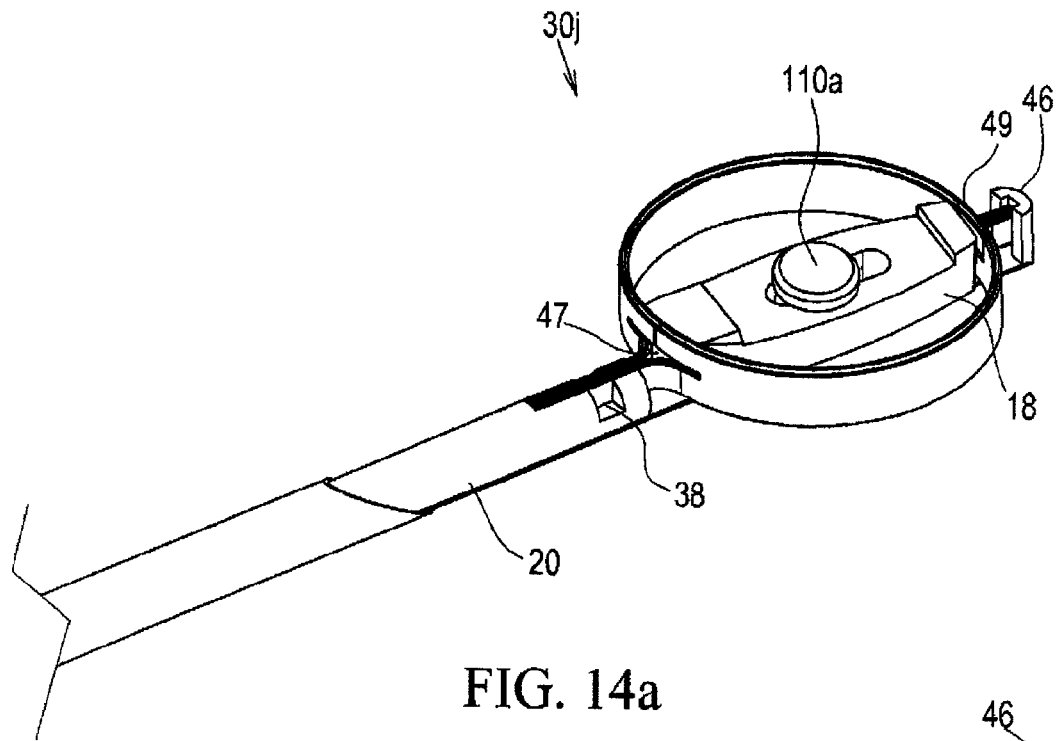
FIG. 14a is a perspective view of the capsulotomy tool of FIG. 12a, showing the burning element in a completely opened configuration, featuring a shaping element connected to the outer tube.
Figure 14B:
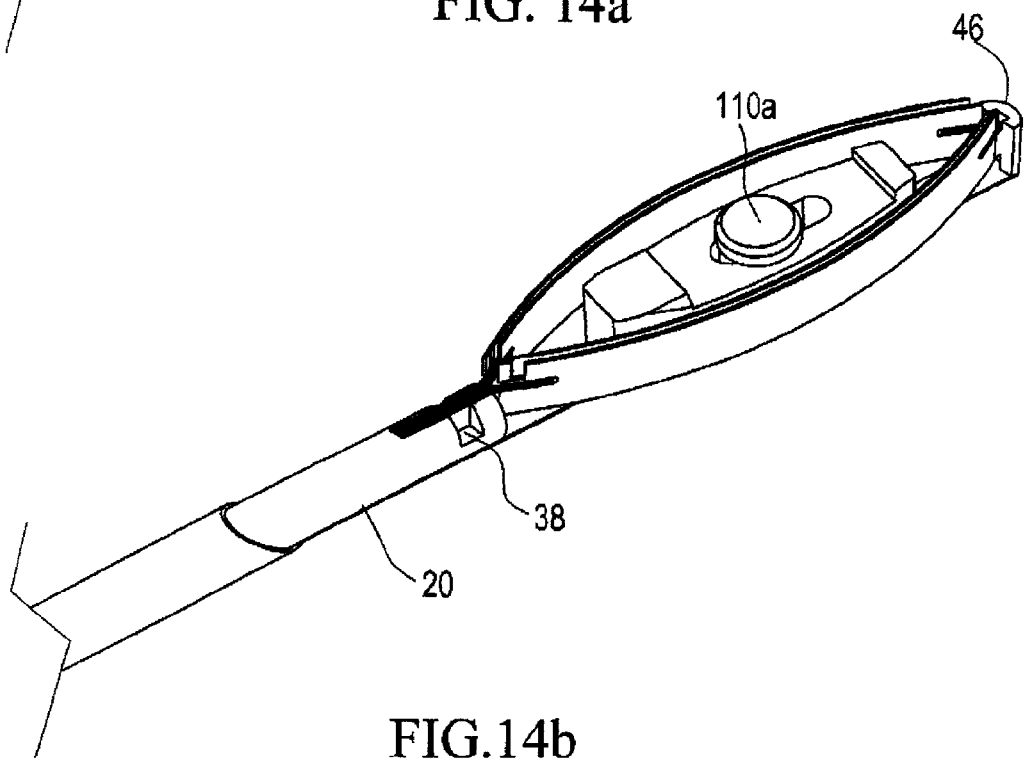
FIG. 14b is a perspective view of the capsulotomy tool of FIG. 12a, showing the burning element in a partially opened configuration, featuring a shaping element connected to the outer tube.

FIG. 14a-b show an alternative embodiment for a capsulotomy tool 10 constructed and operated in accordance with the principles of the present invention, with burning element 30j featuring a shaping element 110a.

FIG. 14b shows shaping element 110 attached to outer tube 18. Shaping element 110 features the same purpose and function as shaping element 110a described above in FIG. 7b.

Figure 15A:
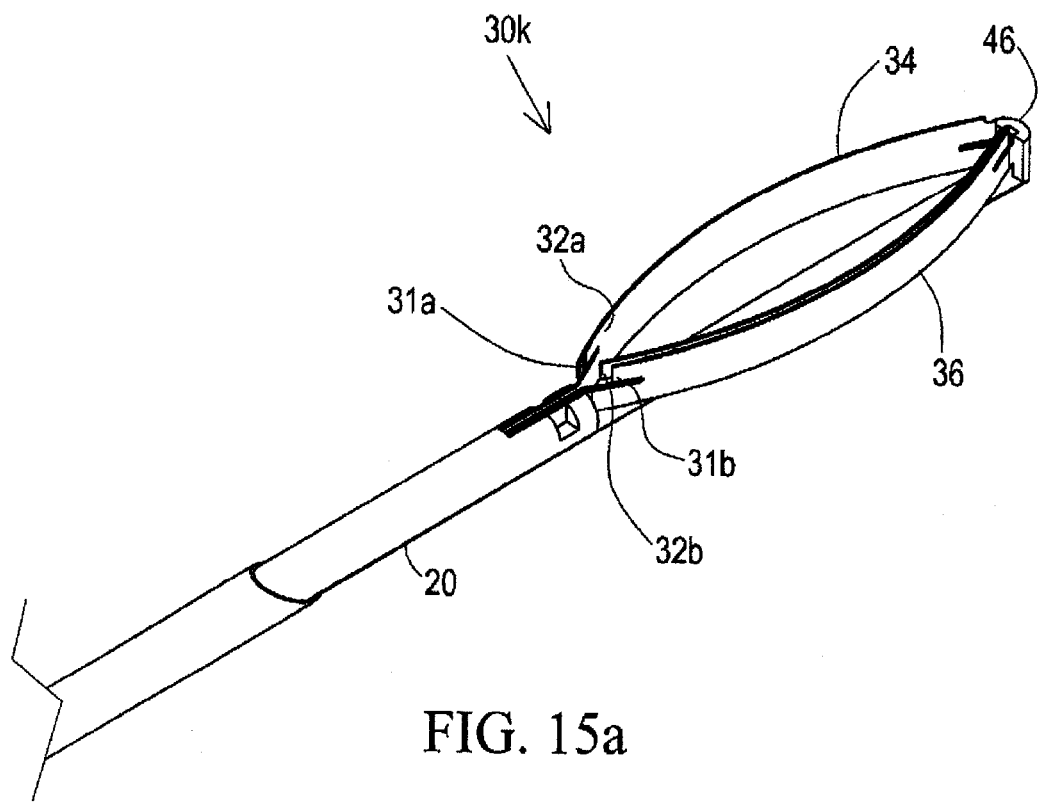
FIG. 15a is a perspective view of a capsulotomy tool, showing the burning element in a partially opened configuration, while the bands are each constructed of two blades, according to a preferred embodiment of the present invention.

FIG. 15a shows an alternative embodiment for a capsulotomy tool 10 constructed and operated in accordance with the principles of the present invention, with the two bands 34, 36 of burning element 30k overlapping each other, and comprising of two blades each 31a, 32a and 31b, 32b, respectively, for the purpose of increasing the heat transfer of blades 31a, 32a and 31b, 32b to achieve a more effective and complete cauterization.

Figure 15B:
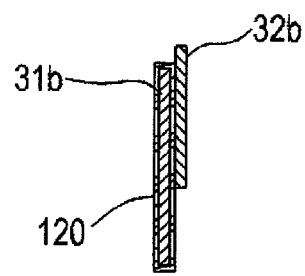
FIG. 15b is a cross-sectional view of one of the bands of the burning element of FIG. 15a, showing the thermal insulation material.

FIG. 15b shows a cross section of band 36 illustrating the width of outer blade 31b is greater than the width of internal blade 32*b*, and blade 32*b* is positioned higher than outer blade 31*b*. The thermal insulation 120 coating blade 31*b* is indicated.

Figure 16A:
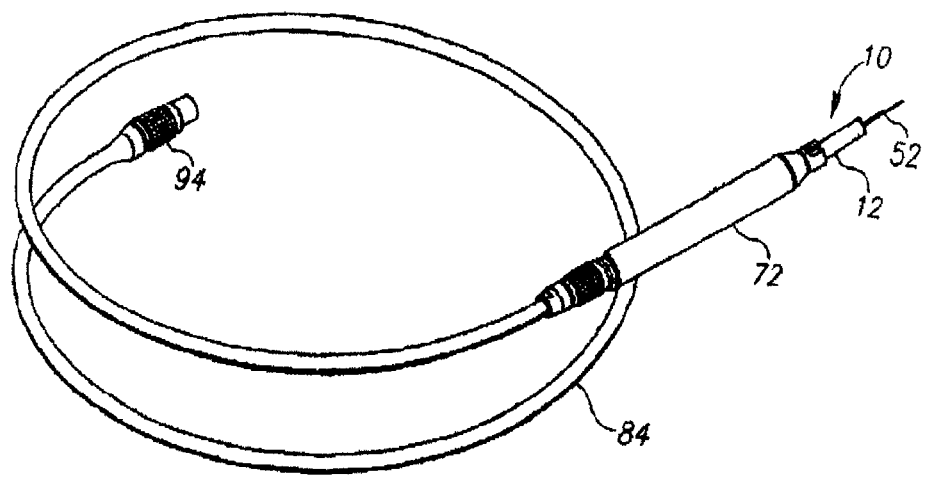
FIG. 16a is a schematic view of part of a system for the performance of a capsulotomy, according to a preferred embodiment of the present invention.
Figure 16B:
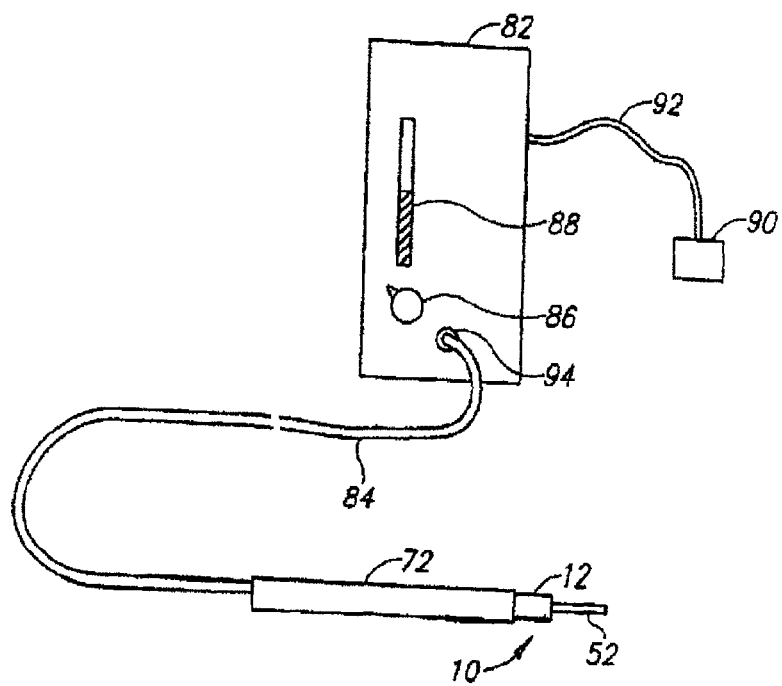
FIG. 16b is a general schematic diagrammatic view of a system for the performance of a capsulotomy, according to a preferred embodiment of the present invention.

Reference is now made to FIGS. 16*a* and 16*b*, and to a system for the performance of a capsulotomy employing the capsulotomy tool described above.

Capsulotomy tool 10 is coupled to a handle 72 which facilitates maneuvering of tool 10 by the surgeon. Handle 72 houses a motor (not shown) that is connected to spring mechanism 54 (see FIG. 2) of main housing 12 for enabling reversible movement of the outer tube 18, the inner rod 20, and the extending and retracting of the burning element 30.

Handle 72 is coupled to a capsulotomy and movement control unit 82 via a power cable 84 having a connector 94 at the end thereof; for supplying electrical current and movement control to capsulotomy tool 10. Capsulotomy and movement control unit 82 also includes a control 86 as well as a display 88 for determining the amount of electrical current applied through power cable 84 to capsulotomy tool 10. Power cable 84 is connected to the motor inside of the handle 72 for facilitating movement of the outer tube 18 and inner rod 20 of capsulotomy tool 10.

A foot-pedal control switch 90 is also connected to capsulotomy and movement control unit 82 via a cord 92. Foot-pedal control switch 90 enables the surgeon to control the movement of the inner and outer tube 20, 18 and the extending and the retracting of the burning element 30, as well as applying of electrical current, with his foot.

Figure 17A:
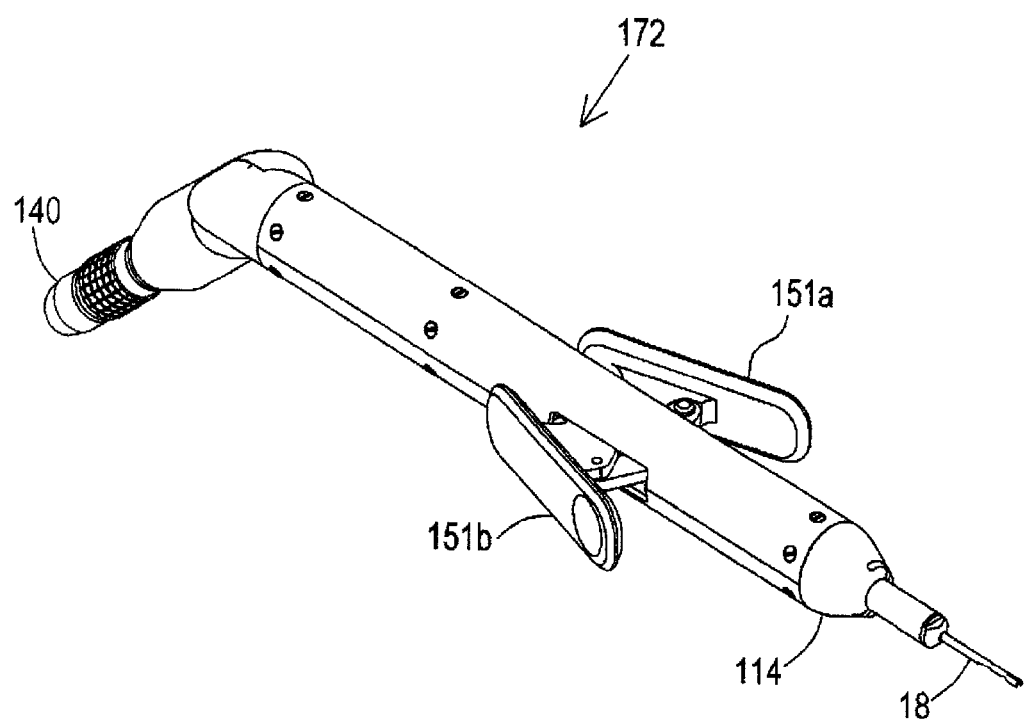
FIGS. 17a-b illustrate a prospective view of an alternative embodiment of part of a system of the present invention.

Referring to FIG. 17 there is shown an alternative embodiment of handle 72 (as shown in FIG. 15). Handle 172 has a pair of finger-depressible actuators 151*a*, 151*b*, situated proximal to distal end 114, opposite from each other. When actuators 151*a-b* are pressed simultaneously by the thumb and index finger of the surgeon, blades 34, 36 are extended to form burning element 30.

Figure 18:
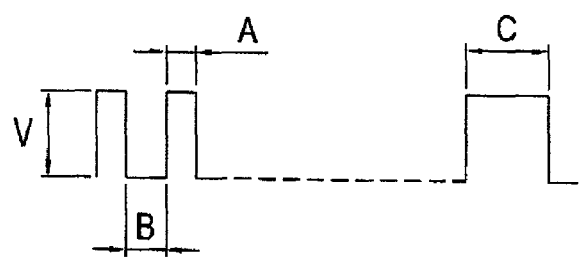
FIG. 18 illustrates a pattern of the wave form representing the electrical pulses.

Referring to FIG. 18 there is shown a pattern of the wave form of the electrical pulses used to heat bands 34, 36. The electrical current flow begins with short duration pulse (A-width), which heats the blades prior to application of duration pulse (C-width) which performs the cauterization.

The short-duration pulses A-width are for the purpose of drying the cauterization area, before the actual cauterization is performed, so that the cauterization is more effective.

There may be one or more short duration A-width pulses, and there may be none. The intervals B between the A-width pulses are varied and are milliseconds long. The entire electrical sequence may be as long as one second or less.

The cauterization may be performed by applying only several of pulses A, and without pulse C. Alternatively, only pulse C is utilized. The Voltage V of the electrical current is approx. 0.6V, at 1-6 Amps.

Operation of capsulotomy tool 10 will now be described, when used for creation of a seared capsulotomy opening during cataract surgery.

Figure 19A:
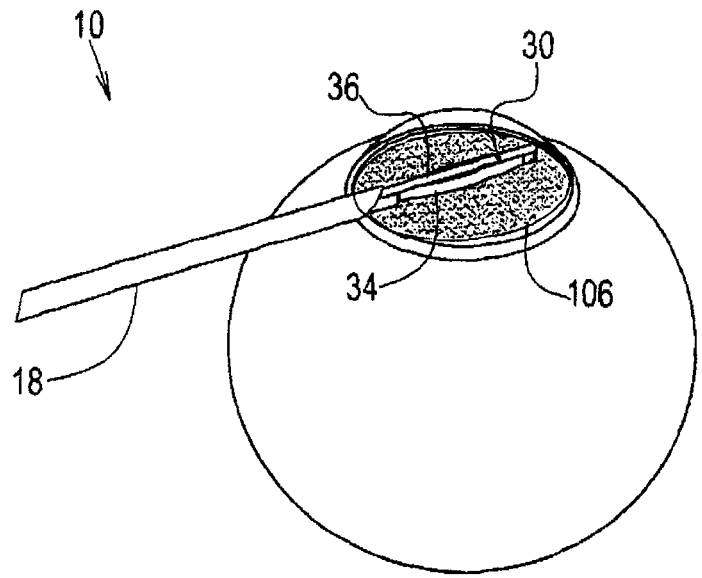
FIGS. 19a-b illustrate the procedure for creating a corneal incision as a first step in cataract surgery.
Figure 19B:
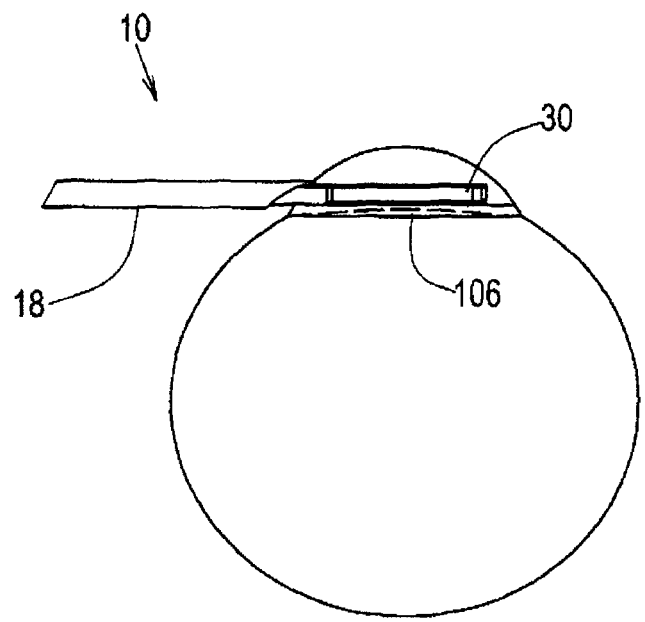
Figure 20:
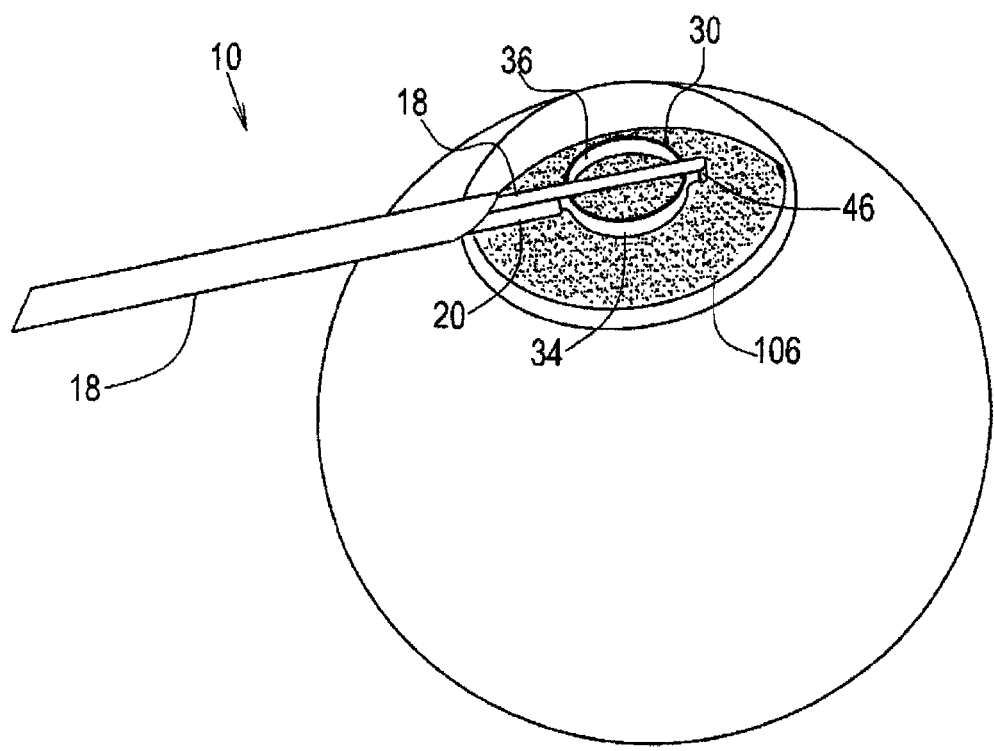
FIG. 20 illustrates the fully expanded circular burning element of the invention positioned upon the lens, moments before searing of the lens for completion of a capsulotomy.
Figure 21:
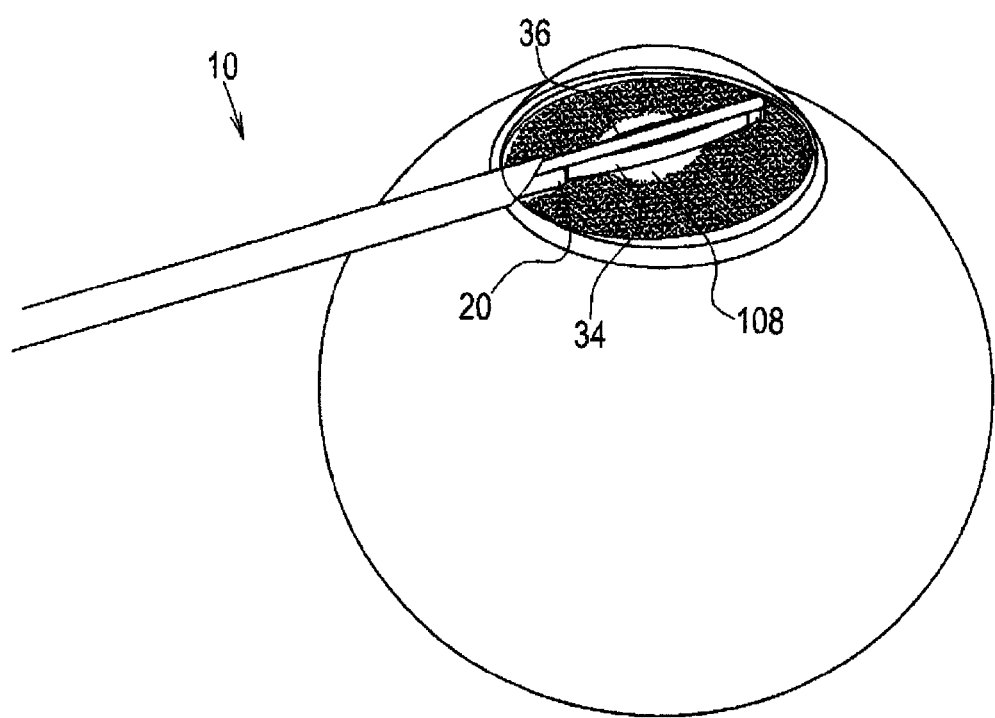
FIG. 21 illustrates the final capsulotomy, and the burning element retracted for removal from the lens.

In FIGS. 19-21, illustrations are schematic and relative sizes are not necessarily accurate. In reality, the capsulotomy opening encompasses approximately half to two thirds of the area of the lens, with the capsulotomy opening usually being within the range of 4-7 mm.

Referring to FIGS. 19*a* and 19*b*, the surgeon first makes a small incision in the cornea 100 of the eye 102, preferably on the order of 1-2 millimeters diameter, using a standard scalpel 104.

Referring to FIG. 20, following formation of an incision in the cornea 100, the end of capsulotomy tool 10 is inserted through the incision, with capsulotomy tool 10 in the configuration shown in FIG. 1. After the eye is entered, inner rod 20 is advanced into outer tube 18 and burning element 30 is extended into its extendable position.

Figure 17B:
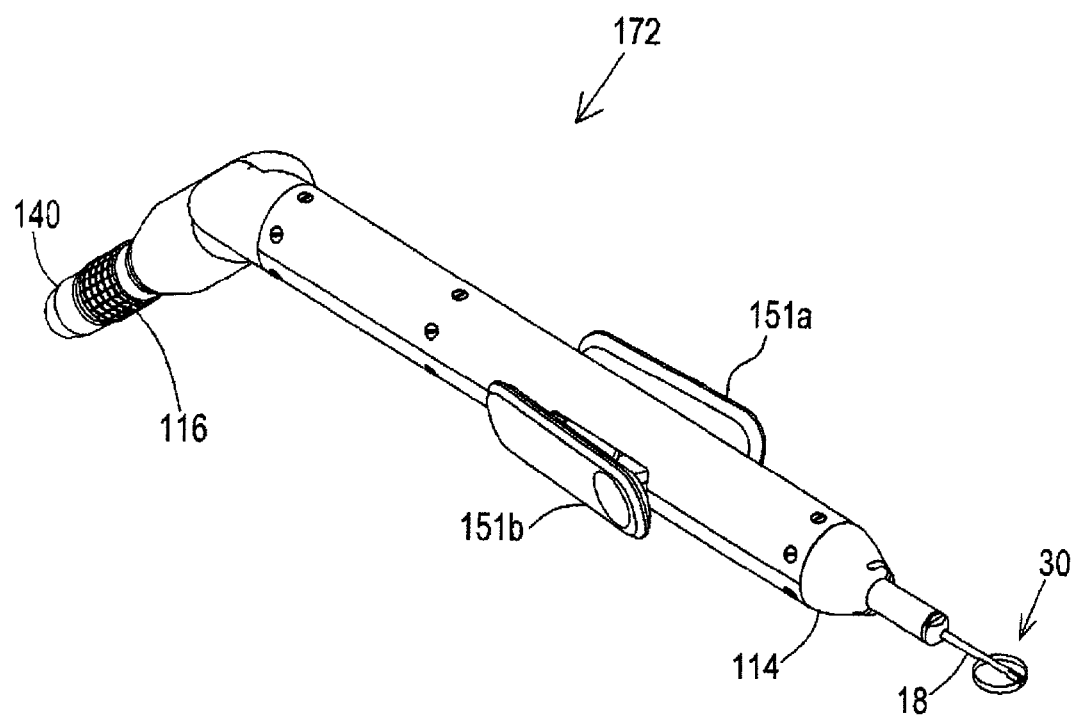

Per the embodiment of FIG. 17*b*, finger-depressible actuators 151*a-b*, inner rod 20 is advanced such that bands 34, 36 of burning element 30 are pushed towards tip 46 of outer tube 18 while outer tube 18 remains stationary. This causes bands 34, 36 of burning element 30 to switch from a substantially flattened configuration (shown in FIG. 3), to a substantially circular configuration (shown in FIG. 17*b*) wherein bands 34, 36 of burning element 30 substantially form a circle with one another (also shown in FIG. 6).

With burning element 30 thus extended and circular, the surgeon lowers tool 10 such that the lens capsule 106 is contacted by bands 34, 36 of burning element 30.

A low-voltage electrical pulse is then applied (see FIG. 18) using foot-pedal control switch 90 (FIG. 16*b*), and bands 34, 36 heat up such that a capsulotomy opening is burned in the lens capsule 106 where bands 34, 36 are positioned.

Referring to FIG. 21, bands 34, 36 are then returned to the retracted configuration via backwards movement of inner rod 20. The capsulotomy opening 108 seared using the invention is apparent in the center of FIG. 22. Closing of bands 34, 36 causes any excess capsular and cortical lens material seared from the area of the capsulotomy 108 to be retained within bands 34, 36, allowing removal of this excess material.

Figure 22:
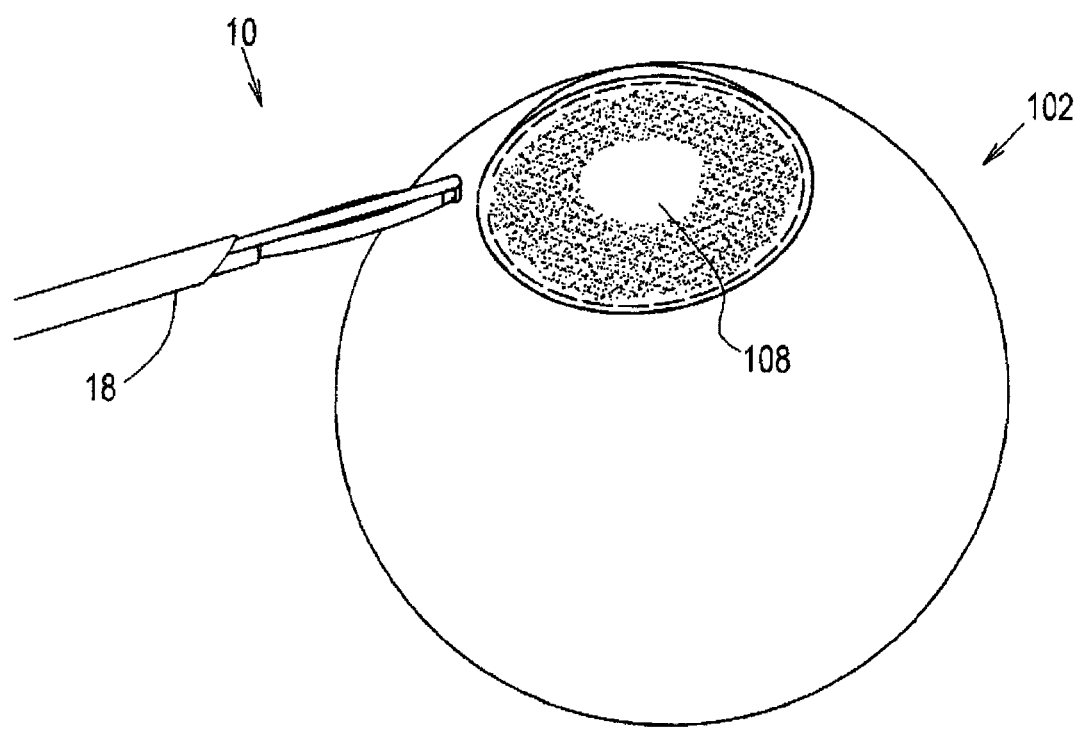
FIG. 22 illustrates the fully retracted tool being removed from the eye, and the final capsulotomy formed.

Referring to FIG. 22, the tool 10 is removed from the eye 102. Apparent at the center of the eye is the final capsulotomy opening 108 formed using the capsulotomy tool and system of the invention. After the tool 10 is removed, the remainder of the cataract surgery can be performed via the capsulotomy opening 108 seared.

Figure 23:
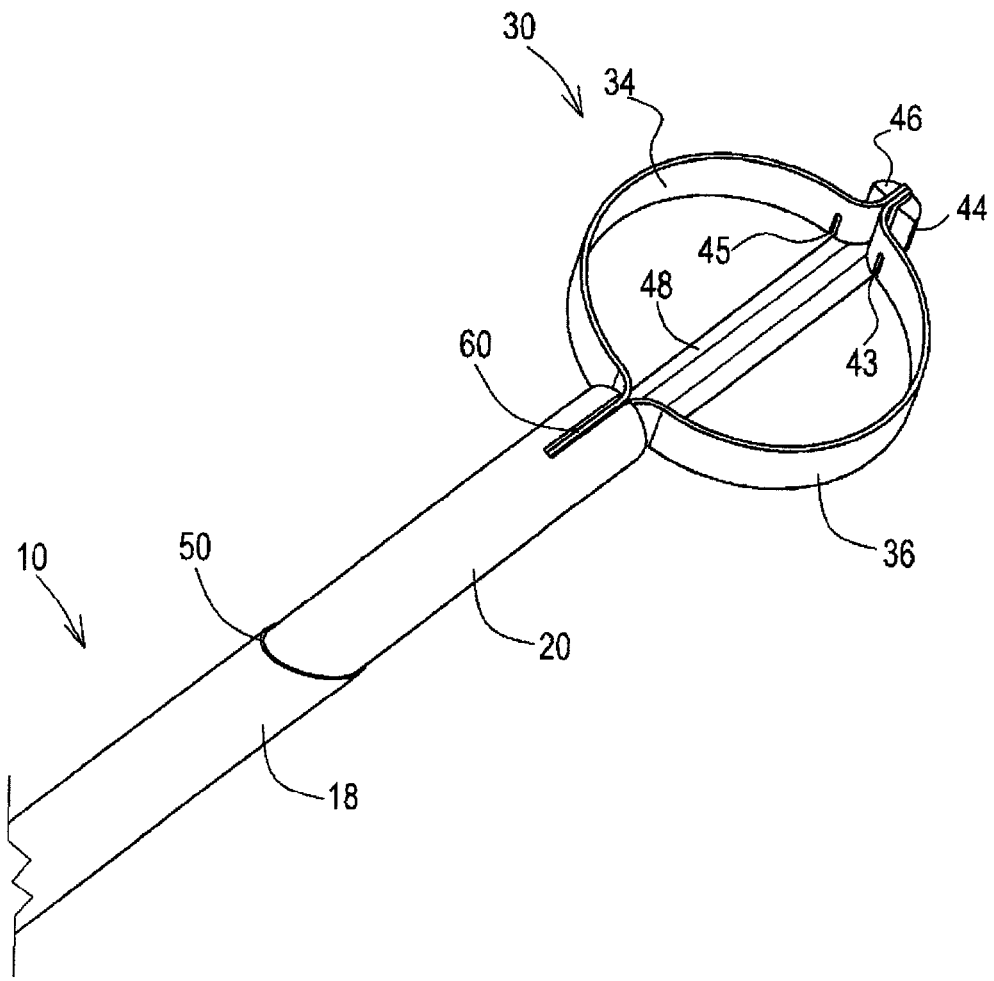
FIG. 23 is a partial view of a capsulotomy tool, showing the burning element in an extended configuration, with each band having a groove defining a predetermined point of weakness.
Figure 24:
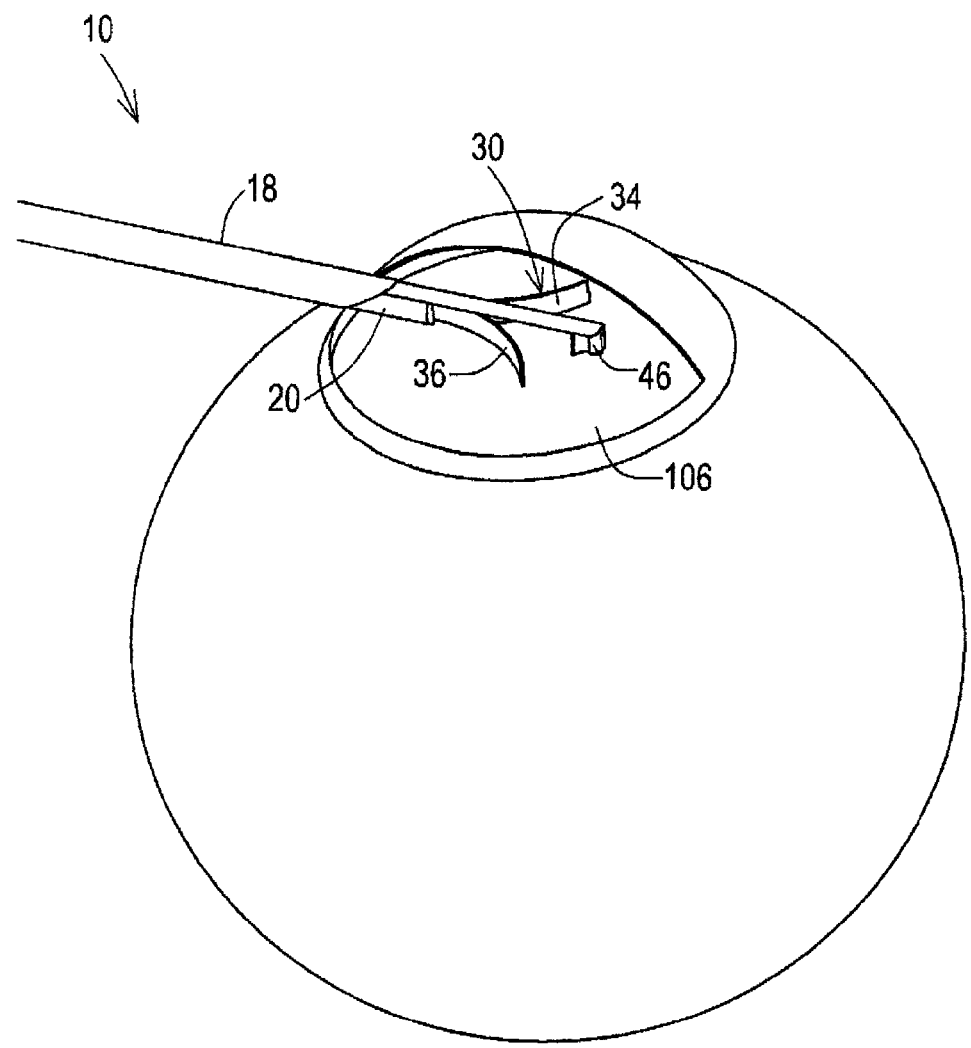
FIG. 24 illustrates the structure of the bands after breaking at predetermined weakness points, while the tool is still in the eye.

FIGS. 23 and 24 describe a solution to a predicament that may occur, in which the electrical current has surged above the desirable range of voltage, and one or both of the bands have broken in a manner that prevents removal of the tool from the eye. Recall that the tool is inserted through a small opening of 1-2 millimeters, and then the burning ring is opened to a larger, circular configuration. Should the burning ring then break in the larger configuration, it is difficult to effect its removal from the eye.

In the event that random breakage has occurred at the center of each band, due to an electrical surge, this breakage can lead to two pairs of band segments (not shown): band segments which remain connected to the end of inner rod 20, and band segments which remain connected to tip 46 of outer tube 18. The band segments remain in loose contact with one another, giving the appearance of being intact. However, when attempts are made to retract the broken bands of the burning element, by effecting pulling of inner rod 20 to within outer tube 18, band segments which remain connected to the end of inner rod 20 may move towards the midline of the tool and can be retracted. However, the band segments which are connected to tip 46 of outer tube 18 remain open and cannot be retracted.

In order to overcome this situation, predefined points of weakness have been designed on the bands of the burning element.

Referring to FIG. 23, each band 34, 36 of burning element 30 has a groove 45, 43, respectively, close to tip 46. When the electrical current is excessive, breakage will occur at the grooves 45, 43, since at these predefined weakness points the decrease in material mass leads to increased resistance to the electrical current, resulting in melting of the metal at grooves 45, 43.

Referring to FIG. 24, bands 34, 36 of burning element 30 are shown after breakage has occurred at the predefined points of weakness (i.e., at grooves 43, 45 at the distal end of the bands). Thus, in this case, as can be seen, bands remain connected to inner rod 20 at the proximal end of the burning element. The overturned arrowhead-shape formed by broken bands 34, 36, allows simple retraction of broken bands 34, 36 from eye 102. Broken bands 34, 36 can be moved toward the midline of the tool, parallel to the horizon, and after retraction into the outer tube 18, broken bands 34, 36 will not protrude beyond the minimal-sized incision made in the eye.

Construction of the aforementioned predefined points of weakness can be applied to all previous embodiments shown.

Thus, the improved design shown in FIGS. 23-24, having predefined points of weakness, preferably present near the distal tip 46, allows for easy removal of the tool after undesirable breakage has occurred in the bands of the burning element.

The system and tool provide an effective and reproducible capsular opening in the lens and allows further steps of cataract surgery, such as phacoemulsification or an equivalent procedure, and removal of cataract material.

Thus, the tool of the present invention provides a very significant advantage when compared with capsulotomy tools of the prior art. The extendable-retractable burning element allows for performance of a capsulotomy in a quick and efficient manner, leaving a capsular opening that is clean and tear resistant. Moreover, the extendable-retractable burning element allows for entry into the eye via a corneal incision on the order of 1-2 millimeters, while allowing for a large capsulotomy, for example, 5-7 millimeters. Using the capsulotomy tool of the present invention, the surgical procedure is simplified.

Using the present invention, a complete circle or a complete oval-shaped searing takes place, so that there is no need for tearing of the lens using forceps, which would be difficult to perform and to control.

Having described the invention with regard to certain specific embodiments thereof, it is to be understood that the description is not meant as a limitation, as further modifications will now become apparent to those skilled in the art, and it is intended to cover such modifications as fall within the scope of the appended claims.

The invention claimed is:

1. A tool for performing a capsulotomy, comprising:
   (a) a main housing having a proximal end and a distal end;
   (b) an extendable-retractable burning element for burning a lens, said burning element being coupled to said distal end of said main housing and adapted for being switched between a retracted configuration and an extended configuration;
   (c) an inner rod extending longitudinally through said main housing and extending from the distal end of said main housing, wherein said burning element is positioned at the end of said inner rod;
   (d) an outer tube that extends longitudinally through said main housing and that extends from said distal end of said main housing, wherein said inner rod is disposed inside of said outer tube, and wherein said inner rod is movable with respect to said outer tube for causing extending and retracting of said burning element;
   (e) a slidable shaping element, connected to said outer tube so that said shaping element is slidable thereon and encompassed by said burning element, said shaping element providing shaping of said burning element; and
   (f) capsulotomy and movement control means coupled to the main housing for providing electrical current to the burning element and movement control for controlling extending and retracting of the burning element, wherein said retractable burning element is insertable into the eye through a small corneal incision when said burning element is in a retracted configuration, and said burning element is adapted to perform a capsulotomy of a predetermined size when it is in an extended configuration and an electrical current is applied to said burning element.

2. The tool of claim 1, wherein said burning element comprises at least one electrically-conductive band generating a circular burn having a closed continuous perimeter, mounted between the end of said inner rod and the tip of said outer tube, and wherein said at least one band having an origination point and a termination point which are both at the same location.

3. The tool of claim 2, wherein a groove is formed on said band, said groove providing a predefined point of weakness allowing for controlled breakage of said burning element at said groove, during an event of excessive electrical current, said groove located adjacent to the distal end of said tool, allowing for retraction of said band in the event of band breakage.

4. The tool of claim 2, wherein said at least one band is formed from any conductive, biocompatible material, such as tungsten alloy.

5. The tool of claim 2, wherein said outer tube comprises a circumferentially truncated extension at the end region thereof, and wherein distal end of said outer tube is bent 90 degrees upwards forming a plate extension soldered to said single band, said plate forcing said band to assume a circular configuration.

6. The tool of claim 1, wherein said burning element comprises a sealed and gapless ring generating a circular burn having a closed continuous perimeter all around, mounted between the end of said inner rod and the tip of said outer tube.

7. The tool of claim 1, wherein said burning element comprises two electrically-conductive bands, said two bands each having an origination point and a termination point respectively connected between the end of said inner rod and the tip of said outer tube.

8. The tool of claim 7, wherein in said retracted configuration, said bands are positioned substantially parallel to one another and above said truncated extension and wherein in said maximally extended configuration, said bands are concavely arched so as to form a substantial circle with one another.

9. The tool of claim 7, wherein said bands have a height greater than the height of said inner rod.

10. The tool of claim 7, wherein in the extended configuration, said bands form a complete circle having a diameter of approximately 4-7 millimeters.

11. The tool of claim 7, wherein said band termination points are joined inwardly.

12. The tool of claim 7, wherein each of said electrically-conductive bands comprises three blades, said blades comprising two outer blades and one middle blade, said bands overlapping each other.

13. The tool of claim 12, wherein said outer blades are coated by a thermal biocompatible insulation material for maintaining a temperature below approximately 41° C.

14. The tool of claim 12, wherein said middle blade is positioned above said outer blades so as to protrude therefrom along its length thereby contacting said lens for effective cauterizing, wherein said middle blade has a reduced width so as to increase the electrical resistance of said middle blade and thus to increase the heat transfer of said middle blade which contacts said lens.

15. The tool of claim 13, wherein the temperature of said outer blades is cooled due to contact of said blades with the viscous material in the eye, and the temperature of said middle blade is maintained high due to the closeness of said outer blades to said middle blade, said closeness not allowing said viscous material to seep between said blades, thus said outer blades function as insulation to said middle blade.

16. The tool of claim 12 wherein each of said three blades has sufficiently low thickness so as to allow flexibility to said blades, said flexibility reducing the risk of crack formation on said blades due to repeated stretching, and said low thickness also resulting in a smaller bending radius causing said burning ring to assume a more circular shape.

17. The tool of claim 16, wherein said inner rod comprises a groove near said origination point, said groove increasing the electrical resistance at said origination point, so as to increase the temperature of said point, so as to achieve proper cauterization.

18. The tool of claim 7 wherein each of said electrically-conductive bands comprises two blades, said blades comprising an outer blade and an inner blade, said bands overlapping each other, wherein said inner blade is positioned above said outer blade.

19. The tool of claim 18, wherein said outer blade is externally coated by a thermal biocompatible insulation material for maintaining a temperature below approximately 41° C.

20. The tool of claim 7, wherein said two electrically-conductive bands overlap each other at said origination points and said termination points, creating a flag shaped region on each end of said burning element, said overlapping allowing generation of a circular burn having a closed continuous perimeter.

21. The tool of claim 1, wherein the outer tube is electrically insulated from the inner rod, and wherein each one of said outer tube and said inner rod defines an opposite pole of an electrical circuit.

22. The tool of claim 1, wherein said outer tube comprises a circumferentially truncated extension at the end region thereof, and wherein said outer tube further comprises a tip at which location said truncated extension ends.

23. The tool of claim 1, wherein said outer tube has a beveled edge located at the interface between said truncated extension and the remainder of said outer tube.

24. The tool of claim 1, wherein movement of said inner rod towards said tip of said outer tube causes said burning element to switch from said retracted configuration to said extended configuration.

25. The tool of claim 1, wherein said burning element is removable prior to use, and can be selected from a variety of sizes of burning elements in order to choose the capsulotomy size.

26. The tool of claim 1, wherein said burning element is capable of searing a capsulotomy having a diameter selected from one of the following diameters: 4 mm, 5 mm, 6 mm and 7 mm.

27. The tool of claim 1, wherein said burning element is capable of searing a complete capsulotomy of a substantially circular shape, without the need for forceps manipulation or tearing of the capsulotomy.

28. The tool of claim 1, wherein said tool is disposable, and is designed for a single use.

29. The tool of claim 1, wherein said slidable shaping element is made of bio-compatible, non-conductive material.

30. The tool of claim 1, wherein said slidable shaping element is insulated by non-conductive material.

31. The tool of claim 1, wherein said slidable shaping element is advanced and pressed against said termination point so as to provide a substantially full-circular shape of said burning element.

32. The tool of claim 1, wherein said slidable shaping element provides an elliptical shape of said burning element.

33. The tool of claim 1, wherein said inner rod has an orientation point marked thereonto, situated on the center of said extended burning element, for the purpose of assisting a user in locating the capsulotomy region.

34. The tool of claim 1, wherein said electrical current is provided in accordance with a waveform comprising at least one relatively short-duration pulse, followed by at least one relatively long-duration pulse.

35. The tool of claim 34, wherein said relatively short-duration pulses comprises variable-time intervals between each other.

36. A system for performing a capsulotomy procedure, comprising;
(a) the capsulotomy tool of claim 1; and
(b) a capsulotomy and movement control unit;
wherein said tool is in connection with said capsulotomy and movement control unit for providing electrical current and movement control to said burning element such that when said burning element is extended and heated, an opening is burned on the lens capsule.

37. The system of claim 36, further comprising a handle connecting between said tool and said capsulotomy and movement control unit.

38. The system of claim 36 wherein said electrical current is provided in accordance with a waveform comprising at least one relatively short-duration pulse, followed by at least one relatively long-duration pulse.

39. The system of claim 38 wherein said relatively short-duration pulses comprises variable-time intervals between each other.

40. The system of claim 38 wherein said waveform comprises said relatively long-duration pulse only.

41. The system of claim 38 wherein said waveform comprises said at least one relatively short-duration pulse only.

42. The system of claim 38 wherein said electrical current is approximately 1-6 amps.

* * * * *